(12) United States Patent
Imamura

(10) Patent No.: US 7,883,862 B2
(45) Date of Patent: Feb. 8, 2011

(54) DIGLYCERIDE SOLUTIONS FOR LIPASE ACTIVITY DETERMINATION

(75) Inventor: Shigeyuki Imamura, Shizuoka (JP)

(73) Assignee: Asahi Kasei Pharma Corporation, Tokyo (JP)

(*) Notice: Subject to any disclaimer, the term of this patent is extended or adjusted under 35 U.S.C. 154(b) by 248 days.

(21) Appl. No.: 11/718,749

(22) PCT Filed: Nov. 18, 2005

(86) PCT No.: PCT/JP2005/021213
§ 371 (c)(1),
(2), (4) Date: May 7, 2007

(87) PCT Pub. No.: WO2006/054681
PCT Pub. Date: May 26, 2006

(65) Prior Publication Data
US 2008/0038765 A1 Feb. 14, 2008

(30) Foreign Application Priority Data

Nov. 19, 2004 (JP) ............................. 2004-335356
Dec. 13, 2004 (JP) ............................. 2004-359872
May 27, 2005 (JP) ............................. 2005-155163

(51) Int. Cl.
*C12Q 1/34* (2006.01)
(52) U.S. Cl. .......................................... 435/18; 435/19
(58) Field of Classification Search ................... 435/18, 435/19
See application file for complete search history.

(56) References Cited

U.S. PATENT DOCUMENTS

| | | | | |
|---|---|---|---|---|
| 4,845,028 A | * | 7/1989 | Imamura et al. ............... 435/15 |
| 5,079,158 A | | 1/1992 | Imamura et al. |
| 5,162,201 A | | 11/1992 | Imamura et al. |
| 5,328,832 A | * | 7/1994 | Miki et al. ..................... 435/19 |
| 5,508,185 A | * | 4/1996 | Kawamura et al. ........... 435/178 |
| 6,261,812 B1 | | 7/2001 | Yamada et al. |
| 6,699,496 B1 | | 3/2004 | Kojima et al. |
| 2003/0104109 A1 | * | 6/2003 | Jacobs et al. ................. 426/602 |
| 2008/0038765 A1 | * | 2/2008 | Imamura ....................... 435/15 |

FOREIGN PATENT DOCUMENTS

| | | |
|---|---|---|
| JP | 59-091898 | 5/1984 |
| JP | 63-245672 | 10/1988 |
| JP | 3-228699 | 10/1991 |
| WO | 99/09119 | 2/1999 |
| WO | 03/029392 | 4/2003 |

OTHER PUBLICATIONS

Fossati P. et al. Kinetic Colorimetric Assay of Lipase in Serum. Clinical Chemistry 38(2)211-215, Feb. 1992.*
English Language Abstract of JP 3-228699.
I. Goldberg et al., "Association of Plasma Lipoproteins with Postheparin Lipase Activities", J. Clin. Invest., vol. 78, pp. 1523-1528 (1986).
Murano et al., "Hepatic Triglyceride Lipase Mass in Patients with Hypertriglyceridemia", The Official Journal of Japanese Society of Laboratory Medicine, vol. 52 / Clinical Chemistry, vol. 33, No. 3, pp. 220 (2004), accompanied by an English language translation thereof.
P. Fossati et al., "Kinetic Colorimetric Assay of Lipase in Serum", Clin. Chem., vol. 38, pp. 211-215 (1992).
M. Ventrucci et al, Int. J. Gastroenterol. 1994, vol. 26, pp. 132-136.

* cited by examiner

*Primary Examiner*—Ralph Gitomer
(74) *Attorney, Agent, or Firm*—Greenblum & Bernstein, P.L.C.

(57) ABSTRACT

Diglyceride solutions for lipase activity determination, comprising at least one diglyceride, a low concentration buffer, and a nonionic surfactant.

21 Claims, 4 Drawing Sheets

[FIG. 1]
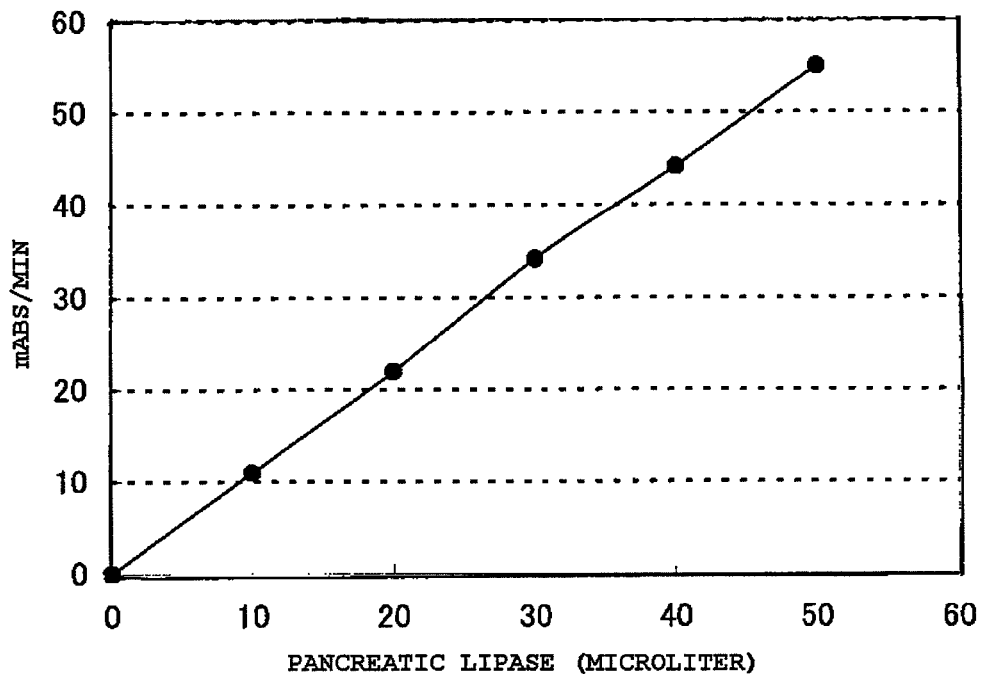
[FIG. 2]
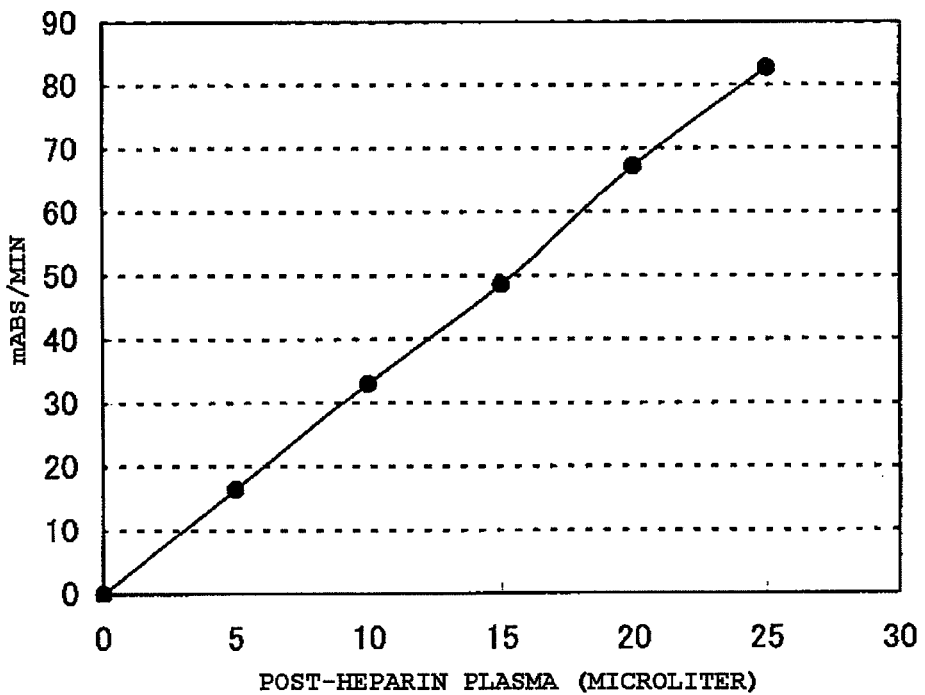

[FIG. 3]
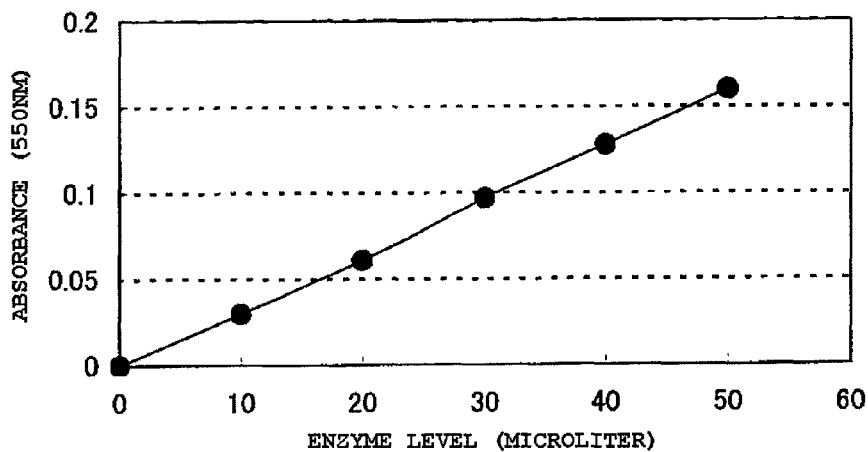
[FIG. 4]
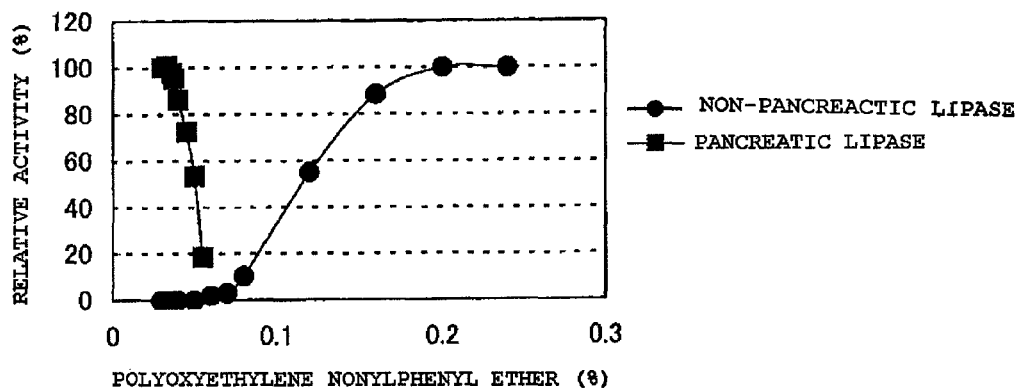

[FIG. 5]
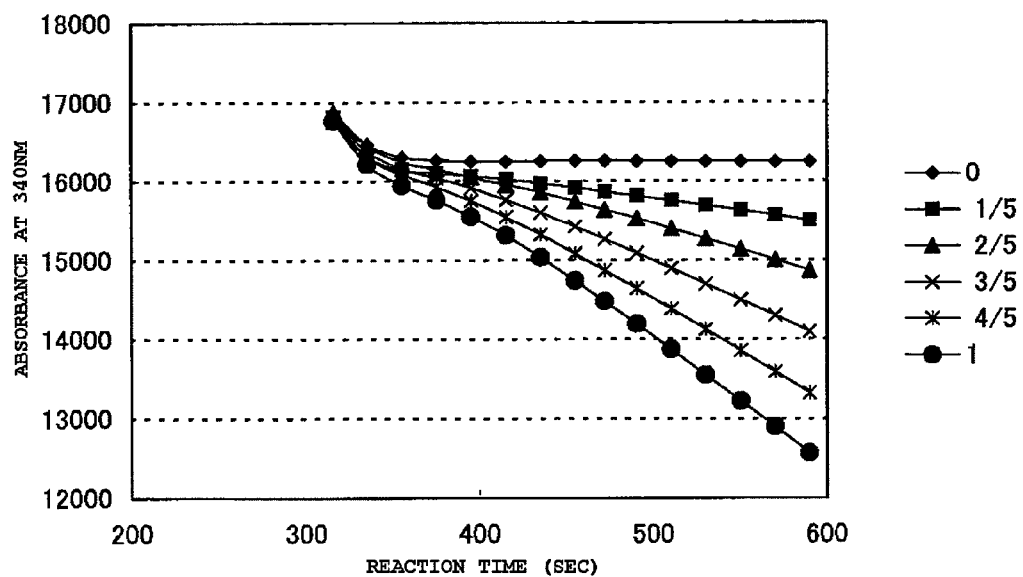
[FIG. 6]
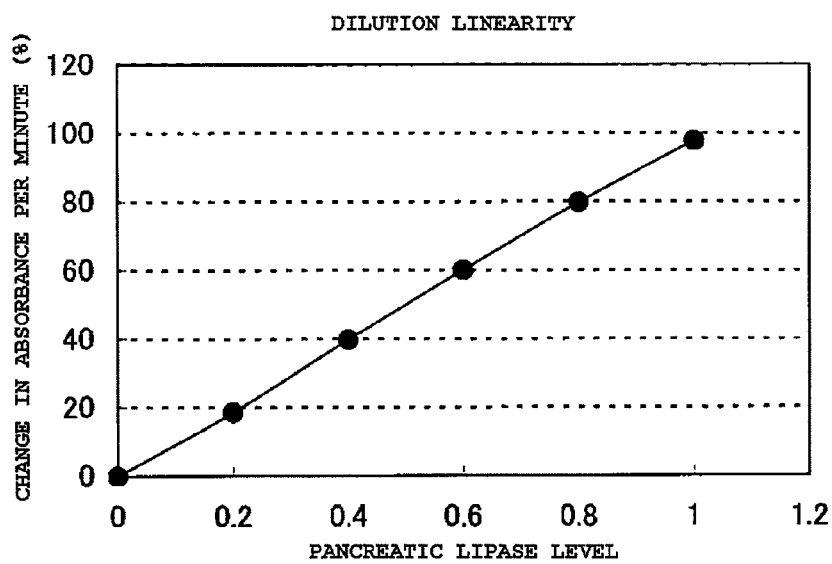

[FIG. 7]
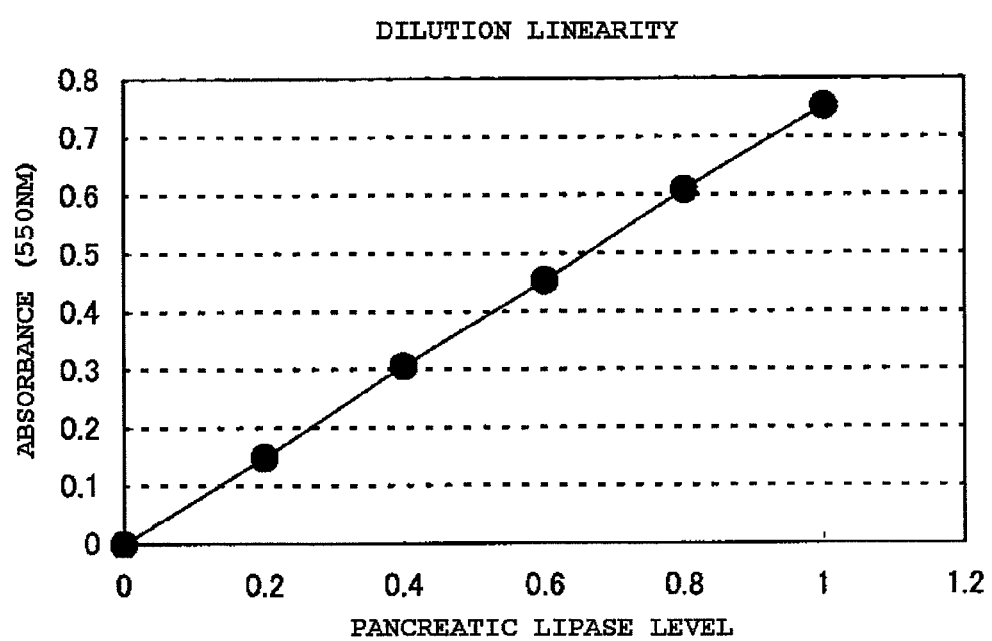

DIGLYCERIDE SOLUTIONS FOR LIPASE ACTIVITY DETERMINATION

TECHNICAL FIELD

The present invention relates to a composition for determining activity of pancreatic lipase or non-pancreatic lipases (such as hepatic lipase or lipoprotein lipase) and a method of determining the activity in the field of clinical laboratory tests.

BACKGROUND ART

Pancreatic lipase in blood is important as a diagnostic marker of pancreatic diseases such as acute pancreatitis and has been employed for ordinary clinical tests.

Meanwhile, hepatic lipase or lipoprotein lipase (hereinafter collectively referred to as non-pancreatic lipases) is an important enzyme in diagnosis of liver diseases or lipid metabolism of lipoprotein. The non-pancreatic lipases play a role in a living body as a conjugate with acidic glycoproteins of the liver or various organs/vascular walls. The non-pancreatic lipases appear in blood by the intravenous injection of heparin or use of heparin during dialysis, or the like, but the activity is extremely low.

Conventionally, in determination of pancreatic lipase activity and/or determination of non-pancreatic lipase activity in blood, a triglyceride has been used as a substrate. The triglyceride has been used in the form of so-called emulsion prepared by emulsifying/dispersing the triglyceride by vigorous stirring in a buffer with gum arabic, polyvinyl alcohol, etc. The lipase activity determination using the substrate has been performed by quantifying a fatty acid liberated by a lipase reaction by the alkalimetry. An attempt to determine fatty acid levels liberated from the lipase substrate in a lipase reaction by the enzymatic method has been performed, but it has been impossible to determine the lipase activity spectrophotometrically using a coupling enzyme system because of strong turbidity of the triglyceride substrate due to an emulsion. Meanwhile, an emulsion substrate has a disadvantage of being likely to cause phase separation during storage, and it has been difficult to determine the lipase activity with good reproducibility. Moreover, in determination of non-pancreatic lipase activity, a triglyceride labeled with a radioactive compound is practically used as a substrate because the activity of non-pancreatic lipases is low in blood than that of pancreatic lipase, and a free fatty acid liberated by a lipase reaction and a substrate triglyceride are separated, followed by determination of the radioactivity of the free fatty acid (Non-Patent Document (1). However, there are many restrictions in handling of a radioactive compound, and the method is not adequate to ordinary clinical tests.

To solve such problems of the method using a triglyceride substrate, methods using a diglyceride as a substrate have been developed (Patent Documents 1 and 2). In the patent documents, 1,2-diglyceride is mainly used as a substrate of lipases. The 1,2-diglyceride is known to change into 1,3-diglyceride by a intramolecular migration reaction of an ester bond, and it has been used so as not to cause the change as much as possible.

Known solutions of a diglyceride in a nonionic surfactant are unstable and cannot be stored for a long period of time. Therefore, in a reagent or a kit using a diglyceride as a substrate, practically, the substrate must be freeze-dried, so a dissolving operation is required before use, resulting in complication in use.

Meanwhile, as described above, it is difficult to determine enzymatic activity of non-pancreatic lipases in a blood sample, so in recent years, a method of determining the protein level of the lipase using a monoclonal antibody by an immunological technique has been performed in the field of clinical laboratory tests (Non-Patent Document 2). However, the immunological technique is used to quantify the protein level of the lipases and has a disadvantage of not determining the enzymatic activity showing the lipase function. Under such circumstances, there has been desired a development of an accurate, sensitive, and easy technique for determining pancreatic lipase or non-pancreatic lipase activity.

[Patent Document 1] JP 59-91898 A
[Patent Document 2] JP 63-245672 A
[Non-Patent Document 1] J.Clin.Invest, 1986, Vol.78, Issue 6, 1523-1528
[Non-Patent Document 2] *The Official Journal of Japanese Society of Laboratory Medicine*, Vol.52/Clinical Chemistry, Vol.33, No.3, 2004, p220

DISCLOSURE OF THE INVENTION

Problems to be Solved by the Invention

An object of the present invention is to provide a composition for lipase activity determination that is in a liquid form and has excellent long-term storage stability. Another object of the present invention is to provide an easy-to-use reagent for lipase activity determination, a kit for lipase activity determination, and a method of determining lipase activity. Specifically, an object is to provide an excellent composition compared with a conventional composition for pancreatic lipase activity determination in the field of clinical laboratory tests, and a method of determining pancreatic lipase activity using the composition. Another object of the present invention is to provide a composition for non-pancreatic lipase activity determination with high sensitivity and specificity to non-pancreatic lipases in a sample, in particular, a blood sample, and a method of determining non-pancreatic lipase activity using the composition easily with high accuracy.

Means for Solving the Problems

In order to determine pancreatic lipase activity stably, the inventor of the present invention first focused attention on stability of 1,2-diglyceride that is now used as a substrate, and then, they found out that the lipase activity changes due to a gradual hydrolysis of 1,2-diglyceride in a reagent during a long storage period and found out that the change makes it difficult to determine pancreatic lipase activity stably and accurately. To solve these problems, the inventor did extensive studies for finding out a diglyceride with excellent stability, and as a result, the inventor found out that a reagent for determining lipase activity stably can be prepared by using diglycerides including a large amount of 1,3-diglyceride converted by treating 1,2-diglyceride in a low-concentration alkaline buffer.

Meanwhile, the inventor of the present invention found out that the diglyceride is useful as a substrate of non-pancreatic lipases and established a novel method of determining non-pancreatic lipase activity which includes: preparing a lipase substrate to be used in determining a non-pancreatic lipase reaction into a clear solution; and determining a product of a lipase reaction by the enzymatic method, thus finding out a high-sensitive and easy determination method. Moreover, the inventor found out a composition for a non-pancreatic lipase reaction and developed a novel method of determining non-pancreatic lipase activity which have excellent specificity and are completely unaffected by pancreatic lipase activity even in a sample containing a component that affects determination of non-pancreatic lipase activity, for example, a sample that contains a component with high pancreatic lipase activity.

To achieve the above-described objects, the inventors of the present invention did extensive studies with focusing on improvement of long-term storage stability of a diglyceride in an aqueous solution, and as a result, the inventor found out that the long-term storage stability is improved by coexistence with a low-concentration buffer, thereby completing the present invention.

That is, the present invention includes the followings:

[A-1] a diglyceride solution for lipase activity determination, which is characterized by including a low-concentration buffer and a nonionic surfactant;

[A-2] a diglyceride solution for lipase activity determination as described in [A-1] above, in which the diglyceride is a mixture of 1,3-diglyceride and 1,2-diglyceride;

[A-3] a composition for lipase activity determination characterized by comprising enzyme(s) that convert a monoglyceride liberated from a diglyceride described in [A-1] or [A-2] above by a lipase reaction into glycerol-3-phosphate via free glycerol;

[A-4] a composition for non-pancreatic lipase activity determination including: (1) Reagent 1 containing at least a high-concentration buffer, monoglyceride lipase, ATP, glycerol kinase, glycerol-3-phosphate oxidase, and peroxidase; and (2) Reagent 2 containing at least a diglyceride solution for lipase activity determination as described in [A-1] or [A-2] above;

[A-5] a composition for non-pancreatic lipase activity determination including: (1) Reagent 1 containing at least a high-concentration buffer, monoglyceride lipase, ATP, glycerol kinase, oxidized NAD or oxidized NADP, glucose, ADP-dependent hexokinase, and glucose-6-phosphate dehydrogenase; and (2) Reagent 2 containing at least a diglyceride solution for lipase activity determination as described in [A-1] or [A-2] above;

[A-6] a composition for non-pancreatic lipase activity determination including: (1) Reagent 1 containing at least a high-concentration buffer, monoglyceride lipase, ATP, glycerol kinase, reduced NAD, phosphoenolpyruvate, pyruvate kinase, and lactate dehydrogenase; and (2) Reagent 2 containing at least a diglyceride solution for lipase activity determination as described in [A-1] or [A-2] above;

[A-7] a composition for non-pancreatic lipase activity determination as described in any one of [A-4] to [A-6] above, in which the concentration of a nonionic surfactant is one that does not allow the expression of lipase activity of pancreatic lipase and causes the expression of lipase activity of non-pancreatic lipases;

[A-8] a composition for non-pancreatic lipase activity determination as described in any one of [A-4] to [A-7] above, in which Reagent 1 and/or Reagent 2 is in a liquid form;

[A-9] a composition for pancreatic lipase activity determination including: (1) Reagent 1 containing at least a diglyceride solution for lipase activity determination as described in [A-1] or [A-2] above, monoglyceride lipase, ATP, glycerol kinase, glycerol-3-phosphate oxidase, and peroxidase; and (2) Reagent 2 containing at least a high-concentration buffer and bile acid or a salt thereof;

[A-10] a composition for pancreatic lipase activity determination including: (1) Reagent 1 containing at least a diglyceride solution for lipase activity determination according to [A-1] or [A-2], monoglyceride lipase, ATP, glycerol kinase, oxidized NAD or oxidized NADP, glucose, ADP-dependent hexokinase, and glucose-6-phosphate dehydrogenase; and (2) Reagent 2 containing at least a high-concentration buffer and bile acid or a salt thereof;

[A-11] a composition for pancreatic lipase activity determination including: (1) Reagent 1 containing at least a diglyceride solution for lipase activity determination as described in [A-1] or [A-2] above, monoglyceride lipase, ATP, glycerol kinase, reduced NAD, phosphoenolpyruvate, pyruvate kinase, and lactate dehydrogenase; and (2) Reagent 2 containing at least a high-concentration buffer and bile acid or a salt thereof;

[A-12] a composition for pancreatic lipase activity determination as described in any one of [A-9] to [A-11] above, in which the concentration of a nonionic surfactant is one that does not allow the expression of lipase activity of non-pancreatic lipases and causes the expression of lipase activity of pancreatic lipase;

[A-13] a composition for pancreatic lipase activity determination as described in any one of [A-9] to [A-12] above, in which Reagent 1 and/or Reagent 2 is in a liquid form;

[A-14] a method of determining non-pancreatic lipase activity using a composition for non-pancreatic lipase activity determination as described in [A-4] above, including: converting a monoglyceride liberated from a diglyceride by a lipase reaction into glycerol by the action of monoglyceride lipase; converting glycerol into glycerol-3-phosphate by glycerol kinase in the presence of ATP; converting glycerol-3-phosphate into hydrogen peroxide by allowing glycerol-3-phosphate oxidase to act; performing a coloring reaction by allowing peroxidase to act in the presence of a dye which colors in the presence of hydrogen peroxide; and determining the increase rate of an absorbance at a wavelength of about 540 to 700 nm;

[A-15] a method of determining non-pancreatic lipase activity using a composition for non-pancreatic lipase activity determination as described in [A-5] above, including: converting a monoglyceride liberated from a diglyceride by a lipase reaction into glycerol by the action of monoglyceride lipase; converting glycerol into ADP by glycerol kinase in the presence of ATP; converting ADP into glucose-6-phosphate by ADP-dependent hexokinase in the presence of glucose; allowing glucose-6-phophate dehydrogenase to act in the presence of oxidized NAD or NADP; and determining the increase rate of an absorbance of reduced NAD or reduced NADP at a wavelength of about 340 nm;

[A-16] a method of determining non-pancreatic lipase activity using a composition for non-pancreatic lipase activity determination as described in [A-6] above, including: converting a monoglyceride liberated from a diglyceride by a lipase reaction into glycerol by the action of monoglyceride lipase; converting glycerol into ADP by glycerol kinase in the presence of ATP; converting ADP into pyruvic acid by pyruvate kinase in the presence of phosphoenolpyruvic acid; allowing lactate dehydrogenase to act in the presence of reduced NAD; and determining the decrease rate of an absorbance of reduced NAD at a wavelength of about 340 nm;

[A-17] a method of determining non-pancreatic lipase activity as described in any one of [A-14] to [A-16] above, in which the concentration of a nonionic surfactant in a composition for lipase activity determination is one that does not allow the expression of lipase activity of pancreatic lipase and causes the expression of lipase activity of non-pancreatic lipases;

[A-18] a method of determining pancreatic lipase activity using a composition for pancreatic lipase activity determination as described in [A-9] above, including: converting a monoglyceride liberated from a diglyceride by a lipase reaction into glycerol by the action of monoglyceride lipase; converting glycerol into glycerol-3-phosphate by glycerol kinase in the presence of ATP; converting glycerol-3-phosphate into hydrogen peroxide by allowing glycerol-3-phosphate oxidase to act; performing a coloring reaction by allowing peroxidase to act in the presence of a dye which colors in the presence of hydrogen peroxide; and determining the increase rate of an absorbance at a wavelength of about 540 to 700 nm;

[A-19] a method of determining pancreatic lipase activity using a composition for pancreatic lipase activity determination as described in [A-10] above, including: converting a monoglyceride liberated from a diglyceride by a lipase reaction into glycerol by the action of monoglyceride lipase; converting glycerol into ADP by glycerol kinase in the presence of ATP; converting ADP into glucose-6-phosphate by ADP-dependent hexokinase in the presence of glucose; allowing glucose-6-phophate dehydrogenase to act in the presence of oxidized NAD or NADP; and determining the increase rate of an absorbance of reduced NAD or reduced NADP at a wavelength of about 340 nm;

[A-20] a method of determining pancreatic lipase activity using a composition for pancreatic lipase activity determination as described in [A-11] above, including: converting a monoglyceride liberated from a diglyceride by a lipase reaction into glycerol by the action of monoglyceride lipase; converting glycerol into ADP by glycerol kinase in the presence of ATP; converting ADP into pyruvic acid by pyruvate kinase in the presence of phosphoenolpyruvic acid; allowing lactate dehydrogenase to act in the presence of reduced NAD; and determining the decrease rate of an absorbance of reduced NAD at a wavelength of about 340 nm;

[A-21] a method of determining pancreatic lipase activity as described in any one of [A-18] to [A-20] above, in which the concentration of a nonionic surfactant in a composition for lipase activity determination is one that does not allow the expression of lipase activity of pancreatic lipase and causes the expression of lipase activity of non-pancreatic lipases;

[A-22] a method of determining lipase activity as described in any one of [A-14] to [A-21] above, in which Reagent 1 and/or Reagent 2 in a composition for lipase activity determination is in a liquid form;

[A-23] a composition for pancreatic lipase activity determination characterized by including at least a nonionic surfactant and a mixture of 1,3-diglyceride and 1,2-diglyceride;

[A-24] a composition for non-pancreatic lipase activity determination characterized by including at least diglyceride;

[A-25] a substrate for lipase activity determination including a low-concentration buffer and diglycerides, in which the concentration of 1,2-diglyceride and 1,3-diglyceride is essentially in an equilibrium state in the presence of a nonionic surfactant;

[A-26] a method of equilibrating 1,2-diglyceride and 1,3-diglyceride;

[B-1] a diglyceride solution for lipase activity determination characterized by including a low-concentration buffer and a nonionic surfactant;

[B-2] a diglyceride solution for lipase activity determination as described in [B-1] above, which is characterized by containing a diglyceride that has been subjected to an alkaline treatment in the presence of a nonionic surfactant;

[B-3] a composition for lipase activity determination including: (1) Reagent 1 containing at least a high-concentration buffer, monoglyceride lipase, ATP, glycerol kinase, glycerol-3-phosphate oxidase, and peroxidase; and (2) Reagent 2 containing at least a diglyceride solution for lipase activity determination as described in [B-1] or [B-2] above;

[B-4] a composition for lipase activity determination including: (1) Reagent 1 containing at least a high-concentration buffer, monoglyceride lipase, ATP, glycerol kinase, oxidized NAD or oxidized NADP, glucose, ADP-dependent hexokinase, and glucose-6-phosphate dehydrogenase; and (2) Reagent 2 containing at least a diglyceride solution for lipase activity determination as described in [B-1] or [B-2] above;

[B-5] a composition for lipase activity determination including: (1) Reagent 1 containing at least a high-concentration buffer, monoglyceride lipase, ATP, glycerol kinase, reduced NAD, phosphoenolpyruvate, pyruvate kinase, and lactate dehydrogenase; and (2) Reagent 2 containing at least a diglyceride solution for lipase activity determination as described in [B-1] or [B-2] above;

[B-6] a composition for lipase activity determination including: (1) Reagent 1 containing at least a low-concentration buffer, monoglyceride lipase, ATP, glycerol kinase, glycerol-3-phosphate oxidase, and peroxidase, a diglyceride solution for lipase activity determination as described in [B-1] or [B-2] above; and (2) Reagent 2 containing at least a high-concentration buffer;

[B-7] a composition for lipase activity determination including: (1) Reagent 1 containing at least a low-concentration buffer, monoglyceride lipase, ATP, glycerol kinase, oxidized NAD or oxidized NADP, glucose, ADP-dependent hexokinase, glucose-6-phosphate dehydrogenase, a diglyceride solution for lipase activity determination as described in [B-1] or [B-2] above; and (2) Reagent 2 containing at least a high-concentration buffer;

[B-8] a composition for lipase activity determination including: (1) Reagent 1 containing at least a low-concentration buffer, monoglyceride lipase, ATP, glycerol kinase, reduced NAD, phosphoenolpyruvate, pyruvate kinase, lactate dehydrogenase and a diglyceride solution for lipase activity determination as described in [B-1] or [B-2] above; and (2) Reagent 2 containing at least a high-concentration buffer;

[B-9] a composition for non-pancreatic lipase activity determination as described in any one of [B-3] to [B-8] above, in which the concentration of a nonionic surfactant is one that does not allow the expression of lipase activity of pancreatic lipase;

[B-10] a composition for pancreatic lipase activity determination as described in any one of [B-3] to [B-8] above, in which the concentration of a nonionic surfactant is one that causes the expression of lipase activity of pancreatic lipase;

[B-11] a method of determining lipase activity which includes: bringing a composition for lipase activity determination as described in [B-3] or [B-6] above into contact with a sample; and determining the increase rate of an absorbance at a visible wavelength;

[B-12] a method of determining non-pancreatic lipase activity which includes: bringing a composition for non-pancreatic lipase activity determination as described in [B-9] above into contact with a sample; and determining the increase rate of an absorbance at a visible wavelength or the increase rate or decrease rate of an absorbance at a wavelength of about 340 nm;

[B-13] a method of determining pancreatic lipase activity which includes: bringing a composition for pancreatic lipase activity determination as described in [B-10] above into contact with a sample; and determining the increase rate of an absorbance at a visible wavelength or the increase rate or decrease rate of an absorbance at a wavelength of about 340 nm;

[B-14] a composition for lipase activity determination as described in [B-3] or [B-6] above characterized by further containing an enzyme that converts a monoglyceride liberated by a lipase reaction from a diglyceride into glycerol-3-phosphate via free glycerol;

[B-15] a composition for lipase activity determination as described in [B-14] above characterized by further containing a Trinder's reagent and a coupler;

[B-16] a composition for non-pancreatic lipase activity determination as described in any one of [B-14] or [B-15] above, in which the concentration of a nonionic surfactant is one that does not allow the expression of lipase activity of pancreatic lipase;

[B-17] a composition for pancreatic lipase activity determination as described in any one of [B-14] or [B-15] above, in which the concentration of a nonionic surfactant is one that causes the expression of lipase activity of pancreatic lipase;

[B-18] a composition for pancreatic lipase activity determination as described in [B-17] above characterized by further containing colipase, and bile acid or a salt thereof;

[B-19] a method of determining lipase activity including: converting a monoglyceride liberated from a diglyceride in a composition for pancreatic lipase activity determination as described in [B-3] above by a pancreatic lipase reaction using the diglyceride as a substrate into glycerol by the action of monoglyceride lipase; converting glycerol into glycerol-3-phosphate by glycerol kinase in the presence of ATP; converting glycerol-3-phosphate into hydrogen peroxide by allowing glycerol-3-phosphate oxidase to act; and determining the increase rate of hydrogen peroxide;

[B-20] a method of determining lipase activity including: converting a monoglyceride liberated from a diglyceride in a composition for lipase activity determination as described in [B-5] above by a pancreatic lipase reaction using the diglyceride as a substrate into glycerol by the action of monoglyceride lipase; converting glycerol into ADP by glycerol kinase in the presence of ATP; converting ADP into pyruvic acid by pyruvate kinase in the presence of phosphoenolpyruvic acid; allowing lactate dehydrogenase to act in the presence of reduced NAD; and determining the decrease rate of an absorbance of reduced NAD at a wavelength of about 300 to 400 nm;

[B-21] a method of determining lipase activity including: converting a monoglyceride liberated from a diglyceride in a composition for lipase activity determination as described in [B-15] above by a pancreatic lipase reaction using the diglyceride as a substrate into glycerol by the action of monoglyceride lipase; converting glycerol into glycerol-3-phosphate by glycerol kinase in the presence of ATP; converting glycerol-3-phosphate into hydrogen peroxide by allowing glycerol-3-phosphate oxidase to act; allowing peroxidase to act in the presence of a dye which colors in the presence of hydrogen peroxide to perform a coloring reaction; and determining the increase rate of an absorbance at a wavelength of about 540-700 nm;

[B-22] a method of determining pancreatic lipase activity as described in [B-19] to [B-21] above, in which the concentration of a nonionic surfactant is one that does not allow the expression of lipase activity of pancreatic lipase;

[B-23] a method of determining pancreatic lipase activity as described in [B-19] to [B-21] above, in which the concentration of a nonionic surfactant is one that causes the expression of pancreatic lipase activity;

[C-1] a composition for pancreatic lipase activity determination which is characterized by containing a diglyceride that has been subjected to an alkaline treatment in the presence of a nonionic surfactant;

[C-2] a composition for pancreatic lipase activity determination as described in [C-1] above characterized by further containing an enzyme that converts a monoglyceride yielded from a diglyceride by a pancreatic lipase reaction into glycerol-3-phosphate via free glycerol;

[C-3] a composition for pancreatic lipase activity determination as described in [C-2] above characterized by containing: monoglyceride lipase, glycerol kinase, pyruvate kinase, and lactate dehydrogenase as enzymes; and further containing ATP, phosphoenolpyruvate, and reduced NAD;

[C-4] a composition for pancreatic lipase activity determination as described in [C-2] above characterized by containing: monoglyceride lipase, glycerol kinase, and glycerol-3-phosphate oxidase as enzymes; and further containing ATP;

[C-5] a composition for pancreatic lipase activity determination as described in [C-4] above characterized by further containing peroxidase, a Trinder's reagent, and a coupler;

[C-6] a composition for pancreatic lipase activity determination as described in any one of [C-1] to [C-5] above characterized by further containing a buffer;

[C-7] a composition for pancreatic lipase activity determination as described in any one of [C-1] to [C-6] above characterized by further containing colipase, and bile acid or a salt thereof;

[C-8] a composition for pancreatic lipase activity determination as described in any one of [C-1] to [C-7] above characterized in that it is divided into at least two reagents;

[C-9] a composition for pancreatic lipase activity determination as described in [C-8] characterized in that glycerol oxidase is added to one reagent, and either or both of glycerol kinase and adenosinetriphosphate are added to any of the other reagents;

[C-10] a method of determining pancreatic lipase activity including: converting a monoglyceride liberated from a diglyceride in a composition for pancreatic lipase activity determination as described in [C-3] above by a pancreatic lipase reaction using the diglyceride as a substrate into glycerol by the action of monoglyceride lipase; converting glycerol into ADP by glycerol kinase in the presence of ATP; converting ADP into pyruvic acid by pyruvate kinase in the presence of phosphoenolpyruvic acid; allowing lactate dehydrogenase to act in the presence of reduced NAD; and determining the decrease rate of an absorbance of reduced NAD at a wavelength of about 300 to 400 nm;

[C-11] a method of determining pancreatic lipase activity including: converting a monoglyceride liberated from a diglyceride in a composition for pancreatic lipase activity determination as described in [C-4] above by a pancreatic lipase reaction using the diglyceride as a substrate into glycerol by the action of monoglyceride lipase; converting glycerol into glycerol-3-phosphate by glycerol kinase in the presence of ATP; converting glycerol-3-phosphate into hydrogen peroxide by allowing glycerol-3-phosphate oxidase to act; and determining the increase rate of hydrogen peroxide;

[C-12] a method of determining pancreatic lipase activity including: converting a monoglyceride liberated from a diglyceride in a composition for pancreatic lipase activity determination as described in [C-5] above by a pancreatic lipase reaction using the diglyceride as a substrate into glycerol by the action of monoglyceride lipase; converting glycerol into glycerol-3-phosphate by glycerol kinase in the presence of ATP; converting glycerol-3-phosphate into hydrogen peroxide by allowing glycerol-3-phosphate oxidase to act; allowing peroxidase to act in the presence of a dye which colors in the presence of hydrogen peroxide to perform a coloring reaction; and determining the increase rate of an absorbance at a wavelength of about 540-700 nm;

[D-1] a composition for non-pancreatic lipase activity determination characterized by containing at least a diglyceride;

[D-2] a composition for non-pancreatic lipase activity determination as described in [D-1] above characterized by further containing an enzyme that converts a monoglyceride yielded from a diglyceride by a non-pancreatic lipase reaction into glycerol-3-phosphate via free glycerol;

[D-3] a composition for non-pancreatic lipase activity determination described in [D-2] above characterized by containing: monoglyceride lipase, glycerol kinase, pyruvate kinase, and lactate dehydrogenase as enzymes; and further containing a nonionic surfactant, ATP, phosphoenolpyruvate, and reduced NAD;

[D-4] a composition for non-pancreatic lipase activity determination as described in [D-2] above characterized by containing: monoglyceride lipase, glycerol kinase, and glycerol-3-phosphate oxidase as enzymes; and further containing a nonionic surfactant and ATP;

[D-5] a composition for non-pancreatic lipase activity determination as described in [D-4] above characterized by further containing peroxidase, a Trinder's reagent, and a coupler;

[D-6] a composition for non-pancreatic lipase activity determination as described in [D-3] to [D-5] above, in which the concentration of a nonionic surfactant is one that does not allow the expression of lipase activity of pancreatic lipase;

[D-7] a composition for non-pancreatic lipase activity determination as described in any one of [D-1] to [D-6] above characterized by further containing a buffer;

[D-8] a composition for non-pancreatic lipase activity determination as described in any one of [D-1] to [D-7] above characterized in that it is divided into at least two reagents;

[D-9] a composition for non-pancreatic lipase activity determination as described in [D-8] characterized in that glycerol oxidase is added to one reagent, and either or both of glycerol kinase and adenosinetriphosphate are added to any of the other reagents;

[D-10] a method of determining non-pancreatic lipase activity characterized by including: converting a monoglyceride liberated from a diglyceride in a composition for non-pancreatic lipase activity determination as described in [D-1] or [D-2] above into glycerol by the action of monoglyceride lipase using the diglyceride as a substrate; and quantifying the glycerol;

[D-11] a method of determining non-pancreatic lipase activity including: converting a monoglyceride liberated from a diglyceride in a composition for lipase activity determination as described in [D-3] above by a non-pancreatic lipase reaction using the diglyceride as a substrate into glycerol by the action of monoglyceride lipase; converting glycerol into ADP by glycerol kinase in the presence of ATP; converting ADP into pyruvic acid by pyruvate kinase in the presence of phosphoenolpyruvic acid; allowing lactate dehydrogenase to act in the presence of reduced NAD; and determining the decrease rate of an absorbance of reduced NAD at a wavelength of about 300 to 400 nm;

[D-12] a method of determining non-pancreatic lipase activity including: converting a monoglyceride liberated from a diglyceride in a composition for lipase activity determination as described in [D-4] above by a non-pancreatic lipase reaction using the diglyceride as a substrate into glycerol by the action of monoglyceride lipase; converting glycerol into glycerol-3-phosphate by glycerol kinase in the presence of ATP; converting glycerol-3-phosphate into hydrogen peroxide by allowing glycerol-3-phosphate oxidase to act; and determining the increase rate of hydrogen peroxide;

[D-13] a method of determining non-pancreatic lipase activity including: converting a monoglyceride liberated from a diglyceride in a composition for lipase activity determination as described in [D-5] above by a non-pancreatic lipase reaction using the diglyceride as a substrate into glycerol by the action of monoglyceride lipase; converting glycerol into glycerol-3-phosphate by glycerol kinase in the presence of ATP; converting glycerol-3-phosphate into hydrogen peroxide by allowing glycerol-3-phosphate oxidase to act; allowing peroxidase to act in the presence of a dye which colors in the presence of hydrogen peroxide to perform a coloring reaction; and determining the increase rate of an absorbance at a wavelength of about 540-700 nm;

[D-14] a method of determining non-pancreatic lipase activity in a sample containing non-pancreatic lipases and pancreatic lipase, which is characterized in that the concentration of a nonionic surfactant is adjusted to suppress the expression of lipase activity of pancreatic lipase;

[D-15] a method of determining non-pancreatic lipase activity using a composition for non-pancreatic lipase activity determination as described in [D-1] to [D-9] above;

[D-16] a method of determining non-pancreatic lipase activity including: converting a monoglyceride liberated from a diglyceride in a composition for non-pancreatic lipase activity determination as described in [D-3] above by a non-pancreatic lipase reaction using the diglyceride as a substrate into glycerol by the action of monoglyceride lipase; converting glycerol into ADP by glycerol kinase in the presence of ATP; converting ADP into pyruvic acid by pyruvate kinase in the presence of phosphoenolpyruvic acid; allowing lactate dehydrogenase to act in the presence of reduced NAD; and determining the decrease rate of reduced NAD; and

[D-17] a method of determining non-pancreatic lipase activity including: converting a monoglyceride liberated from a diglyceride in a composition for non-pancreatic lipase activity determination as described in [D-5] above by a non-pancreatic lipase reaction using the diglyceride as a substrate into glycerol by the action of monoglyceride lipase; converting glycerol into glycerol-3-phosphate by glycerol kinase in the presence of ATP; converting glycerol-3-phosphate into hydrogen peroxide by allowing glycerol-3-phosphate oxidase to act; allowing peroxidase to act in the presence of a dye which colors in the presence of hydrogen peroxide to perform a coloring reaction; and determining the increase rate of the coloring.

Effect of the Invention

A reagent for lipase activity determination and a composition for lipase activity determination that are easy to use and are excellent in reproducibility and accuracy can be provided, and an aqueous solution of a diglyceride having excellent long-term storage stability can be provided. Meanwhile, pancreatic lipase activity can be determined with high reproducibility and accuracy. Moreover, non-pancreatic lipase activity in a sample, a blood sample in particular, can be determined sensitively and easily with high accuracy and specificity.

BRIEF DESCRIPTION OF THE DRAWINGS

[FIG. 1] The results of dilution linearity of pancreatic lipase based on Example 1-5 of the present invention.

[FIG. 2] The results of dilution linearity of non-pancreatic lipases based on Example 1-6 of the present invention.

[FIG. 3] The results of dilution linearity of non-pancreatic lipases based on Example 2-5 of the present invention.

[FIG. 4] The results showing effects of a nonionic surfactant on pancreatic lipase and non-pancreatic lipases based on Example 2-6 of the present invention. In this graph, the symbols "●" and "■" mean non-pancreatic lipases and pancreatic lipase, respectively.

[FIG. 5] The time course of a pancreatic lipase reaction based on Reaction Formula 1.

[FIG. 6] The results of dilution linearity of pancreatic lipase based on Reaction Formula 1.

[FIG. 7] The results of dilution linearity of pancreatic lipase based on Reaction Formula 3.

BEST MODE FOR CARRYING OUT THE INVENTION

Hereinafter, the present invention will be specifically described.

A diglyceride aqueous solution having excellent long-term storage stability, a method of stabilizing long-term storage of a diglyceride aqueous solution, a method of storing a diglyceride aqueous solution stably during distribution of the present invention are useful for various products containing the solution, such as a composition for lipase activity determination having excellent long-term storage stability and a reagent for lipase activity determination. In addition, they are useful for a method of stabilizing long-term storage of a composition for lipase activity determination and a reagent for lipase activity determination and a method of stabilizing long-term storage of a composition for lipase activity determination and a reagent for lipase activity determination during distribution and/or storage.

A composition for lipase activity determination, a reagent for lipase activity determination, and a method of determining lipase activity of the present invention are useful for accurate and easy determination of lipase activity in a sample, in particular, accurate and easy determination of pancreatic lipase or non-pancreatic lipase activity in a sample in the field of clinical laboratory tests.

A composition for lipase activity determination of the present invention is an easy-to-use composition for lipase activity determination characterized by containing a diglyceride solution having remarkably improved long-term storage stability during distribution and/or storage, etc. by coexistence with a low-concentration buffer to improve long-term stability of a diglyceride substrate dissolved in a nonionic surfactant. Moreover, the composition is characterized in that a low-concentration buffer coexists with a diglyceride substrate that has been subjected to an alkaline treatment in the presence of a nonionic surfactant. Furthermore, the composition is characterized in that the concentration of a nonionic surfactant is adjusted to an appropriate concentration depending on the type of lipase to be determined (pancreatic lipase or non-pancreatic lipase).

A method of determining lipase activity of the present invention is characterized in that a monoglyceride liberated by the action of pancreatic lipase or non-pancreatic lipases on the substrate is enzymatically detected.

A substrate of a lipase to be used in the present invention may be obtained by: previously preparing a phospholipid such as 1,2-dioleoylglyceryl choline, 1-palmitoyl-2-oleyl glyceryl choline, egg yolk-derived purified lecithin, or soybean-derived purified lecithin; and allowing phospholipase C to act on the phospholipid, but preferable examples thereof include 1,2-diglyceride yielded by a reaction of phospholipase C with a phospholipid such as lecithin. Meanwhile, diglycerides (a mixture of 1,2-diglyceride and 1,3-diglyceride) in which part of the 1,2-diglyceride has been converted into 1,3-diglyceride by an alkaline treatment in the presence of a nonionic surfactant may be used as substrates of a lipase reaction of the present invention. From the viewpoint of yielding more stable lipase activity, the mixture of 1,2-diglyceride and 1,3-diglyceride is preferable as a lipase substrate, and in another aspect, a mixture in which 1,2-diglyceride and 1,3-diglyceride are approximately in the equilibrium state is preferable. The diglyceride mixture may be yielded by an alkaline treatment using a buffer containing a nonionic surfactant while changing the temperature and heating time. The alkaline treatment temperature and alkaline treatment time can be appropriately set based on the measured ratio of 1,2-diglyceride and 1,3-diglyceride. Specifically, the ratio of 1,2-diglyceride and 1,3-diglyceride is preferably in the range of 2:1 to 2:3, or is preferably in the range of 1:1 to 2:3. Meanwhile, in another aspect, the ratio is preferably in the range of 2:1 to 1:1. Moreover, the ratio of 1,2-diglyceride and 1,3-diglyceride is preferably in the range of 70:30 to 30:70, or is preferably in the range of 50:50 to 30:70. Meanwhile, in another aspect, the ratio of 1,2-diglyceride and 1,3-diglyceride is preferably in the range of 70:30 to 50:50. In addition, in another aspect, the ratio of 1,2-diglyceride and 1,3-diglyceride is preferably in the range of 50:50 to 35:65. Examples of a condition for achieving an equilibrium state of 1,2-diglyceride and 1,3-diglyceride include: in the case of pH 8 to pH 9, a heating method at 37° C. for about 5 to 8 hours, at 30° C. for about 10 to 20 hours; and in the case of pH 9 to pH 11, a heating method at 37° C. for about 1 hour. In the case of pH 9 to pH 11, a heating method at 37° C. for about 1 hour is more preferable. Moreover, in another aspect, in the case of pH 8 to pH 9, a heating method at 37° C. for about 5 to 8 hours or at 30° C. for about 10 to 20 hours is more preferable. In the case of pH 8 to pH 9, the upper limit of pH is preferably lower than pH 9.0, more preferably pH 8.7 or lower, further preferably pH 8.5 or lower, while the lower limit of pH is preferably pH 8.0 or higher, more preferably 8.1 or higher, further preferably pH 8.3 or higher, particularly preferably pH 8.4 or higher. Meanwhile, in the case of pH 9 to pH 11, the upper limit of pH is preferably pH 11.0 or lower, more preferably pH 10.7 or lower, further preferably pH 10.5, particularly preferably pH 10.3 or lower, most preferably pH 10.25 or lower, while the lower limit of pH is preferably pH 9.0 or higher, more preferably 9.4 or higher, further preferably pH 9.5 or higher, particularly preferably pH 9.7 or higher, most preferably pH 9.8 or higher. The substrate solution thus prepared is preferably put in cold storage for long-term storage. The substrate is used in a lipase reaction solution described below.

Meanwhile, according to the present invention, there is provided a liquid substrate for lipase activity determination containing diglycerides, in which the concentration distribution of 1,2-diglyceride and 1,3-diglyceride is essentially in an equilibrium state in the presence of a low-concentration buffer and a nonionic surfactant. The concentration distribution in an equilibrium state is not particularly limited as long as it is a proportion of 1,2-diglyceride and 1,3-diglyceride whenever the ratio of 1,2-diglyceride and 1,3-diglyceride is not changed under a certain temperature condition, but specifically examples include a state where a diglyceride mixture is subjected to the above-described alkaline treatment and then stored at 4° C. to 8° C. In the case where the mixture is stored at 4 to 8° C., the ratio of 1,2-diglyceride and 1,3-diglyceride is not changed. In the case where the mixture is put in cold storage, it can be used at a pH in the range of 5 to 9.5, and the upper limit is preferably pH 9.5 or lower, more preferably pH 9.0 or lower, further preferably pH 8.5 or lower, particularly preferably pH 8.3 or lower, most preferably pH 8.1 or lower, while the lower limit is preferably pH 5.0 or higher, more preferably pH 6.0 or higher, further preferably pH 7.0 or higher, particularly preferably pH 7.5 or higher, most preferably pH 7.8 or higher. In another aspect, the pH during cold storage is preferably about pH 8.

Note that, as a method of determining the ratio of 1,2-diglyceride and 1,3-diglyceride, an analysis is performed by the Yatoro scanning method (detection is performed by FID; Flame Ionization Scanning method) after development by thin layer chromatography (developing solvent; 95% chloroform : 5% acetone).

The optimum substrate concentration for a lipase reaction is in the range of 0.25 mM to 2 mM, and about 0.5 mM is particularly preferable in view of stability and specificity to a lipase. For the concentration of a raw material diglyceride to be used in the present invention, the lower limit is preferably 0.25 mM or more, further preferably 0.30 mM or more, particularly preferably 0.32 mM or more, most preferably 0.34 mM or more. Meanwhile, the upper limit is preferably 0.5 mM or less, further preferably 0.4 mM or less, particularly preferably 0.38 mM or less, most preferably 0.36 mM or less. In particular, about 0.35 mM is preferable in view of stability and specificity to pancreatic lipase. As a concentration of a diglyceride to be used in the present invention, an optimum concentration for a non-pancreatic lipase reaction may be selected, and the lower limit is preferably 0.25 mM or more, more preferably 0.30 mM or more, particularly preferably 0.32 mM or more, most preferably 0.5 mM or more. Meanwhile, the upper limit is preferably 2 mM or less, further preferably 1 mM or less, particularly preferably 0.8 mM or less, most preferably 0.6 mM or less. In particular, about 0.5 mM is preferable in view of stability and specificity to pancreatic lipase. In general, a substrate having higher affinity to an enzyme is preferable as a substrate for enzyme activity determination because a certain level of enzyme activity can be achieved even if the substrate is decreased during storage. The indicator of the affinity is a Km value. The Km value of pancreatic lipase to 1,2-diglyceride is $1.1 \times 10^{-3}$ M, while the Km value of a substrate containing 1,2-diglyceride and 1,3-diglyceride at a ratio of 1:1 is $2.3 \times 10^{-3}$ M, so a substrate containing 1,3-diglyceride is more preferable. Moreover, a substrate containing a large amount of 1,3-diglyceride is more preferable.

A fatty acid as a higher fatty acid residue in a diglyceride may be a higher fatty acid having 12 or more carbon atoms, and examples thereof include: saturated higher fatty acids such as lauric acid, myristic acid, palmitic acid, stearic acid, and arachidic acid; and unsaturated higher fatty acids such as palmitoleic acid, oleic acid, linoleic acid, linolenic acid, and arachidonic acid. Such higher fatty acids may be used singly or in combination of different two of them, and a diglyceride containing unsaturated higher fatty acid(s) is more preferable because a solution of the diglyceride prepared as substrate has high clarity. Particularly preferable examples of the diglyceride include 1,2-dioleylglycerol and 1-palmitoyl-2-oleylglycerol. Those diglycerides may be yielded by: previously preparing a phospholipid such as 1,2-dioleoylglyceryl choline, 1-palmitoyl-2-oleyl glyceryl choline, egg yolk-derived purified lecithin, or soybean-derived purified lecithin; and allowing phospholipase C to act on the phospholipid.

In the present invention, a nonionic surfactant to be used for yielding a liquid composition for lipase activity determination having excellent long-term stability may be selected from a polyoxyethylene (POE) higher alcohol ether, a POE secondary alcohol ethoxylate, a POE alkylphenyl ether, a POE fatty acid ester, a POE sorbitan fatty acid ester, etc., and in terms of solubility and stability, a POE alkylphenyl ether nonionic surfactant is preferable. Examples of the POE alkylphenyl ether nonionic surfactant include POE nonylphenyl ether.

In the case of pancreatic lipase, the concentration of a nonionic surfactant used may be in the range where pancreatic lipase activity is expressed at a maximum level and is not inhibited, that is, in the range of 1.5 to 2.5-fold molar ratio with respect to a raw material diglyceride, and 2-fold molar ratio is particularly preferable. In the case of non-pancreatic lipases, if components that affect on determination of non-pancreatic lipase activity are absent in a sample, the concentration may be a general one, and specifically, it should be 1.5-fold molar ratio or more with respect to a diglyceride. In the case where pancreatic lipase is present in a sample as a component that affects on determination of non-pancreatic lipase activity, the concentration is preferably adjusted to a concentration where lipase activity of pancreatic lipase is not expressed and a lipase reaction of non-pancreatic lipases is not inhibited. In adjusting the concentration, the molar ratio of a nonionic surfactant to a diglyceride should be adjusted to a ratio other than about 1.5 to 2 molar, and it is preferably 2.5-fold molar or more, more preferably 3-fold molar or more, further preferably 4-fold molar or more, particularly preferably 5-fold molar or more. From the aspect of actual operations, a specific lower limit is preferably 0.08% (% by weight) or more, more preferably 0.10% or more, further preferably 0.15% or more, particularly preferably 0.20% or more. Meanwhile, from the aspect of actual operations, a specific upper limit is preferably 2% (% by weight) or less, more preferably 1% or less, further preferably 0.5% or less, particularly preferably 0.3% or less. For example, the range of the concentration is preferably 0.15% to 2%, particularly preferably 0.2 to 0.3%.

Essentially, with a focus on a water-soluble micelle structure that is formed depending on the molar ratio of a diglyceride and a nonionic surfactant, a nonionic surfactant should be used at least in an amount required for forming a micelle structure different form one that is formed in the case of a diglyceride: nonionic surfactant=about 1:2. Meanwhile, a nonionic surfactant and a diglyceride may be used at a molar ratio in the range of 10 to 30-fold molar ratio where pancreatic lipase activity is not expressed and non-pancreatic lipase activity is expressed, and they are particularly preferably used at a molar ratio of 15 to 20-fold.

In the present invention, examples of a buffer to be used for achieving long-term stability of a diglyceride dissolved in a surfactant include: a Good's buffer such as Tris-HCl, TES, HEPES, TAPSO, POPSO, Tricine, or Bicine; and glycine-NaOH buffer. Of those, from the viewpoint of a low reagent blank, Tricine and Bicine are more preferable, and Bicine is particularly preferable. The concentration of the buffer used may be about an equimolar to 2-fold molar to the diglyceride concentration.

The long-term stability of a diglyceride dissolved in a surfactant depends on the concentration of a coexistent buffer, so it is extremely important to select the concentration of the buffer. In the case where the concentration of a buffer to be added to a diglyceride dissolved in a nonionic surfactant is a high concentration, for example, 10 mM or more, the diglyceride is unstable at room temperature and is hydrolyzed even if it is put in a cold storage. To maintain long-term storage stability of a diglyceride, the concentration of a buffer is preferably used in the range of 0.5 to 9 mM. The range is more preferably 2 to 7 mM, particularly preferably 3 to 5 mM. Therefore, if necessary, additional measures such as division of a reagent is very preferable for a composition for lipase determination in view of long-term stability of a solution containing a diglyceride and a surfactant, and the type of lipase to be determined, etc.

A composition for lipase activity determination of the present invention may have the following six modes.

(A) The composition includes: (1) Reagent 1 containing at least a high-concentration buffer, monoglyceride lipase, ATP, glycerol kinase, glycerol-3-phosphate oxidase, and peroxidase; and (2) Reagent 2 containing at least a diglyceride solution for lipase activity determination as described in [A-1] or [A-2] above.

As described above, a lipase substrate, i.e., a diglyceride is preferably used in a low-concentration buffer, but the concentration of the other buffer containing no substrate may be selected freely. A high-concentration buffer is essential to acquire reproducibility of a lipase reaction. The lower limit of the concentration of a buffer used is preferably 50 mM or more, more preferably 100 mM or more, further preferably 150 mM or more, particularly preferably 180 mM or more. Meanwhile, the upper limit is preferably 500 mM or less, more preferably 300 mM or less, further preferably 250 mM or less, particularly preferably 220 mM or less, most preferably about 200 mM.

In the case of pancreatic lipase, the optimum pH of a buffer is 7.8 to 8.1, while in the case of non-pancreatic lipases, the optimum pH of a buffer is 7.7 to 8.3. There may be used a buffer having a pH buffering ability in the pH range, such as a Good's buffer including Tris-HCl, TES, HEPES, TAPSO, POPSO, Tricine, or Bicine. Of those, from the viewpoint of a low reagent blank, Tricine and Bicine are more preferable, and Bicine is particularly preferable.

(B) The composition includes: (1) Reagent 1 containing at least a low-concentration buffer, monoglyceride lipase, ATP, glycerol kinase, glycerol-3-phosphate oxidase, peroxidase, and the above-described diglyceride solution for lipase activity determination; and (2) Reagent 2 containing at least a high-concentration buffer. Note that, the best modes of monoglyceride lipase, glycerol kinase, glycerol-3-phosphate oxidase, peroxidase, and other components will be described in detail in Reaction Formula 3 below.

(C) The composition includes: (1) Reagent 1 containing at least a high-concentration buffer, monoglyceride lipase, ATP, glycerol kinase, oxidized NAD or oxidized NADP, glucose, ADP-dependent hexokinase, and glucose-6-phosphate dehydrogenase; and (2) Reagent 2 containing at least the above-described diglyceride solution for lipase activity determination.

(D) The composition includes: (1) Reagent 1 containing at least a low-concentration buffer, monoglyceride lipase, ATP, glycerol kinase, oxidized NAD or oxidized NADP, glucose, ADP-dependent hexokinase, glucose-6-phosphate dehydrogenase, and the above-described diglyceride solution for lipase activity determination; and (2) Reagent 2 containing at least a high-concentration buffer. Note that, the best modes of monoglyceride lipase, glycerol kinase, ADP-dependent hexokinase, and glucose-6-phosphate dehydrogenase will be described in detail in Reaction Formula 2 below.

(E) The composition includes: (1) Reagent 1 containing at least a high-concentration buffer, monoglyceride lipase, ATP, glycerol kinase, reduced NAD, phosphoenolpyruvate, pyruvate kinase, and lactate dehydrogenase; and (2) Reagent 2 containing at least the above-described diglyceride solution for lipase activity determination.

(F) The composition includes: (1) Reagent 1 containing at least a low-concentration buffer, monoglyceride lipase, ATP, glycerol kinase, reduced NAD, phosphoenolpyruvate, pyruvate kinase, lactate dehydrogenase, and the above-described diglyceride solution for lipase activity determination; and (2) Reagent 2 containing at least a high-concentration buffer. Note that, the best modes of the enzymes used in (E) and (F), that is, monoglyceride lipase, glycerol kinase, pyruvate kinase, and lactate dehydrogenase will be described in detail in Reaction Formula 1 below.

In the case of using a diglyceride as a substrate, products of a lipase reaction are a free fatty acid and a monoglyceride. The lipase activity can be determined by determining a production rate of the free fatty acid or monoglyceride with coupling of enzymatic reactions using a spectroscopic technique, but a free fatty acid is present in blood, in particular, it is present at a high concentration in serum after dialysis or the intravenous injection of heparin. Therefore, it is more preferable to determine a monoglyceride, instead, by the enzymatic method. In quantification of the monoglyceride, determination is preferably performed by the enzymatic method using a coupling enzyme involved in the monoglyceride.

Methods of quantifying a monoglyceride by the enzymatic method include the following methods shown in the following reaction formula.

In the following reaction formula, MGLP is monoglyceride lipase, GK is glycerol kinase, ATP is adenosinetriphosphate, ADP is adenosinediphosphate, PEP is phosphoenolpyruvate, NADH is reduced β-diphosphopyridine nucleotide, NAD is oxidized β-diphosphopyridine nucleotide, ADP-HK is ADP-dependent hexokinase, and G6PDH is glucose-6-phosphate dehydrogenase. GPO is glycerol-3-phosphate oxidase, POD is peroxidase, 4-AA is 4-aminoantipyrine, and TOOS is ethyl-N-(2-hydroxy-3-sulfopropyl)-m-toluidine sodium salt.

[Chem 1]

Reaction Formula 1

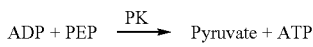

-continued

Reaction Formula 2

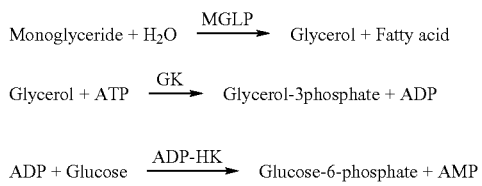

[Chem 2]

Reaction Formula 3

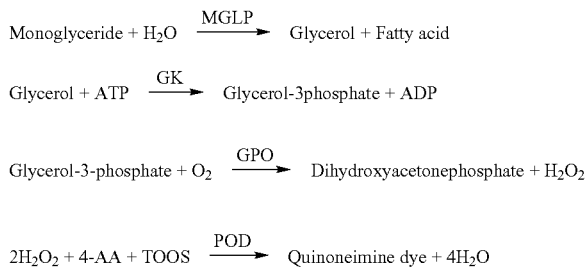

[Chem 3]

$$2H_2O_2 + 4\text{-}AA + TOOS \xrightarrow{POD} \text{Quinoneimine dye} + 4H_2O$$

First, Reaction Formula 1 will be described.

The origin of monoglyceride lipase to be used in the present invention is not particularly limited as long as the enzyme does not act on a diglyceride and acts specifically on a monoglyceride, but from the viewpoint of stable supply, an enzyme derived from a microorganism is preferable. In particular, an enzyme derived from the genus *Bacillus* is preferable. The lower limit of the concentration of monoglyceride lipase to be used as a coupling enzyme in a lipase reaction is preferably 0.5 U/ml or more, more preferably 0.6 U/ml or more, further preferably 0.7 U/ml or more, particularly preferably 0.72 U/ml or more, very preferably 0.74 U/ml or more. The upper limit is about 5 U/ml, and is preferably 3 U/ml or less, more preferably 1.13 U/ml or less, further preferably 1 U/ml or less, particularly preferably 0.8 U/ml or less, very preferably 0.78 U/ml or less, particularly very preferably 0.76 U/ml or less. It is most preferably about 0.75 U/ml.

The origin of glycerol kinase to be used in the present invention is not particularly limited, but an enzyme having excellent stability is preferably used. In particular, an enzyme derived from the genus *Flavobacterium* is preferable. The lower limit of the concentration of glycerol kinase to be used as a coupling enzyme in a pancreatic lipase reaction is preferably 0.1 U/ml or more, more preferably 0.15 U/ml or more, further preferably 0.18 U/ml or more, particularly preferably 0.2 U/ml or more. Meanwhile, the upper limit is about 2 U/ml, and is preferably 1 U/ml or less, more preferably 0.5 U/ml or less, further preferably 0.3 U/ml or less, particularly preferably 0.22 U/ml or less. It is most preferably about 0.2 U/ml.

As pyruvate kinase to be used in the present invention, there may be used an enzyme derived from muscles of animals that are generally used as a raw material of a reagent for clinical laboratory tests. The concentration of pyruvate kinase to be used as a coupling enzyme in a pancreatic lipase reaction should be about 0.5 to 10 U/ml, and is preferably in the range of 1 to 2 U/ml, particularly preferably in the range of 0.8 to 1.2 U/ml. It is most preferably about 1 U/ml. The concentration of phosphoenolpyruvate to be used in the present invention as a substrate of pyruvate kinase is in the range of 0.3 to 2 mM, preferably 0.3 to 0.4 mM, otherwise 0.48 to 0.52 mM, and it is preferably about 0.5 mM.

The origin of lactate dehydrogenase to be used in the present invention is not particularly limited, but an enzyme having excellent stability and derived from chicken heart is more preferably used. The concentration of the enzyme to be used as a coupling enzyme in a pancreatic lipase reaction should be about 0.15 to 1.5 U/ml, and is preferably in the range of 0.3 to 0.4 U/ml, otherwise 0.28 to 0.32 U/ml. It is preferably about 0.3 U/ml.

The concentration of reduced NAD to be used in the present invention as a substrate of lactate dehydrogenase is preferably in the range of 0.2 to 0.4 mM, further preferably in the range of 0.2 to 0.35 mM, particularly preferably in the range of 0.28 to 0.32 mM. It is preferably about 0.3 mM. In another aspect, it is preferably in the range of 0.3 to 0.4 mM.

A composition prepared by further adding magnesium ion that serves as an activator of glycerol kinase and pyruvate kinase to a composition of the present invention is very preferable. The concentration of the magnesium ion should be in the range of 1.5 to 4 mM, and is preferably in the range of 1.8 to 2.2 mM, and it is particularly preferably about 2 mM. As the magnesium ion, a salt such as magnesium sulfate or magnesium acetate may be used, and magnesium sulfate is particularly preferable.

To maintain pH of a lipase reaction to a certain level, use of a buffer is very preferable. The optimum pH of pancreatic lipase is pH 7.7 to 8.1, while the optimum pH of non-pancreatic lipases is pH 7.7 to 8.3, and there may be used a buffer having pH buffering ability in the pH ranges, such as a Good's buffer including Tris-HCl, TES, HEPES, TAPSO, POPSO, Tricine, and Bicine. In particular, from the viewpoint of a low reagent blank, Tricine and Bicine are more preferable, and Bicine is particularly preferable. The lower limit of the concentration of a buffer used is preferably 50 mM or more, more preferably 100 mM or more, further preferably 150 mM or more, particularly preferably 180 mM or more. Meanwhile, the upper limit is preferably 500 mM or less, more preferably 300 mM or less, further preferably 250 mM or less, particularly preferably 220 mM or less. It is most preferably about 200 mM.

Next, Reaction Formula 2 will be described.

In the composition of a reagent for lipase determination using Reaction Formula 2, the buffers, monoglyceride lipase, glycerol kinase, and ATP are the same as those in Reaction Formula 1 above. ADP that is one of products of glycerol kinase can be converted into glucose-6-phosphate by ADP-dependent hexokinase (ADP-HK) in the presence of glucose. The origin of ADP-HK is not particularly limited, but from the viewpoint of stable supply, an enzyme derived from a microorganism is preferable. In particular, an extremely thermophilic bacteria-derived enzyme belonging to the genus *Pyrococcus, Thermococcus*, etc. is particularly preferable. The concentration of glucose that is a substrate of ADP-HK may be in the range of 2 to 50 mM, and is preferably in the range of 10 to 30 mM, particularly preferably in the range of 15 to 25 mM. The concentration of the enzyme used as a coupling enzyme in a lipase reaction may be in the range of 0.2 to 3 U/ml, and is particularly preferably in the range of 0.4 to 1 U/ml. Glucose-6-phosphate that is a product of the enzyme can be converted into reduced NAD or NADP by glucose-6-phosphate dehydrogenase in the presence of oxidized NAD or NADP. The origin of glucose-6-phosphate dehydrogenase is not particularly limited, but from the viewpoint of stable supply, an enzyme derived from a microorganism is preferable. In particular, an enzyme derived from the genus *Leuconostoc* is particularly preferable. The concentration of the enzyme used as a coupling enzyme in a lipase reaction may be in the range of 0.2 to 3 U/ml, and is particularly preferably in the range of 0.4 to 1 U/ml.

Next, Reaction Formula 3 will be described.

In the composition of a reagent for lipase determination using Reaction Formula 1, the buffers, monoglyceride lipase, glycerol kinase, and ATP are the same as those in Reaction Formula 1 above. Glycerol-3-phosphate that is one of products of glycerol kinase can be converted into hydrogen peroxide by glycerol-3-phosphate oxidase that specifically oxidizes glycerol-3-phosphate. The origin of glycerol-3-phosphate oxidase is not particularly limited, and from the viewpoint of stable supply, an enzyme derived from a microorganism is preferable. In particular, an enzyme derived from a lactic acid bacterium is particularly preferable. The concentration of the enzyme used as a coupling enzyme in a pancreatic lipase reaction may be in the range of 2 to 50 U/ml, and is particularly preferably in the range of 5 to 20 U/ml. Hydrogen peroxide yielded by a reaction of glycerol-3-phophate oxidase produces a dye by oxidative condensation of peroxidase, a chromogen of Trinder's reagent, and a coupler. As the chromogen of a Trinder-type reagent, there may be used phenol derivative(s), aniline derivative(s), toluidine derivative(s), etc., and specific examples thereof include N,N-dimethylaniline, N,N-diethylaniline, 2,4-dichlorophenol, N-ethyl-N-(2-hydroxy-3-sulfopropyl)-3,5-dimethoxyaniline (DAOS), N-ethyl-N-sulfopropyl-3,5-dimentylaniline (MAPS), N-ethyl-N-(2-hydroxy-3-sulfopropyl)-3,5-dimethylaniline (MAOS), N-ethyl-N-(2-hydroxy-3-sulfopropyl)-m-toluidine (TOOS), N-ethyl-N-sulfopropyl-m-anisidine (ADPS), N-ethyl-N-sulfopropylaniline (ALPS), N-ethyl-N-sulfopropyl-3,5-dimethoxyaniline (DAPS), N-sulfopropyl-3,5-dimethoxyaniline (HDAPS), N-ethyl-N-sulfopropyl-m-toluidine (TOPS), N-ethyl-N-(2-hydroxy-3-sulfopropyl)-m-anisidine (ADOS), N-ethyl-N-(2-hydroxy-3-sulfopropyl)-aniline (ALOS), N-(2-hydroxy-3-sulfopropyl)-3,5-dimethoxyaniline (HDAOS), and N-sulfopropyl-aniline (HALPS) (manufactured by Dojindo Laboratories). The concentration of the chromogen used in a reagent for pancreatic lipase activity determination may be in the range of 0.02 to 0.5%, and is particularly preferably in the range of 0.05 to 0.1%. As the coupler, a coupler such as 4-aminoantipyrine or 3-methyl-2-benzothiazolinone hydrazone (MBTH) may be used. The concentration of the coupler used in a reagent for pancreatic lipase determination may be in the range of 0.02 to 0.5%, and is particularly preferably in the range of 0.05 to 0.1%.

Meanwhile, hydrogen peroxide can develop a color with a leuco-type reagent in the presence of peroxidase. Specific examples of the reagent include o-dianisidine, o-tolidine, 3,3-diaminobenzidine, 3,3,5,5-tetramethylbenzidine; manufactured by Dojindo Laboratories, N-(carboxymethylaminocarbonyl)-4,4-bis(dimethylamine)biphenylamine (DA64), and 10-(carboxymethylaminocarbonyl)-3,7-bis(dimethylamino)phenothiazine (DA67); manufactured by Wako Pure Chemical Industries, Ltd.

The origin of peroxidase to be used in the present invention is not particularly limited, but an enzyme derived from horseradish is particularly preferable because it has been stably supplied. The concentration of the enzyme used as a coupling enzyme in a lipase reaction may be in the range of 2 to 50 U/ml, and is particularly preferably in the range of 5 to 20 U/ml.

Meanwhile, hydrogen peroxide can be quantified by a fluorescence method, an analysis method using chemiluminescence, a method of quantifying an aldehyde yielded from an alcohol, or an electrode method. The fluorescence method may be performed using a compound that emits fluorescence by oxidation, such as homovanillic acid, 4-hydroxyphenylacetate, tyramine, paracresol, or a diacetyl fluorescein derivative, while the chemiluminescence method may be performed by using, as a catalyst, luminol, lucigenin, isoluminol, pyrogallol, etc. Examples of a method of producing an aldehyde from an alcohol using a catalase or the like and quantifying the resultant aldehyde include: a method using a Hantzsch reaction, a method of developing a color by a condensation reaction with MBTH, and a method using aldehyde dehydrogenase.

Meanwhile, in the case of determining hydrogen peroxide using electrodes, the materials of the electrodes are not particularly limited as long as they can transfer electrons from and to hydrogen peroxide, and examples thereof include platinum, gold, and silver. The determination method using electrodes include known methods such as amperometry, potentiometry, and coulometry, and an electron mediator may be used to mediate a reaction between an oxidase or a substrate and electrodes, followed by determination of the resultant oxidation or reduction current or the electrical quantity thereof. As the electron mediator, any substance having electron transfer function can be used, and examples thereof include substances such as ferrocene derivatives and quinone derivatives. Meanwhile, en electron mediator may be used to mediate between hydrogen peroxide yielded by an oxidase reaction and electrodes, followed by determination of the resultant oxidation or reduction current or the electrical quantity thereof.

A composition for lipase activity determination of the present invention may be used as one reagent containing all the components, but is preferably used as two reagents of Reagent 1 (R1) and Reagent 2 (R2). In the case of Reaction Formula 1, R1 is preferably a reagent containing, for example, ATP, phosphoenolpyruvate, monoglyceride lipase, glycerol kinase, pyruvate kinase, and lactate dehydrogenase, and it may further contain calcium ion, magnesium ion, ammonium ion, a Good's buffer, etc. The R1 or R2 in Reaction Formulae 1 to 3 all contain diglyceride as a lipase substrate dissolved in a nonionic surfactant. To maintain long-term storage stability of a diglyceride in a liquid form without denaturation, the concentration of a buffer in R2 is extremely important. The type of the buffer may be selected from Good's buffers such as acetate buffer, citrate buffer, Tris-HCL buffer, MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, CHES, CAPSO, and CAPS. The concentration of the buffer used may be in the range of 0.5 to 10 mM, and is preferably in the range of 1 to 5 mM, particularly preferably in the range of 1.5 to 2 mM. Meanwhile, in the case of determination of pancreatic lipase, R2 is preferably a reagent containing bile acid or a salt thereof and reduced NAD, and it may further contain a Good's buffer, etc. Bile acid is preferably deoxycholic acid, taurodeoxycholic acid, or glycodeoxycholic acid, more preferably deoxycholic acid. Such taurodeoxycholic acid, glycodeoxycholic acid, and deoxycholic acid are particularly preferably in the forms of sodium salts because of higher solubility. The salt of bile acid is not limited to a sodium salt, and potassium salts or the like are also preferable.

A biogenic substance such as serum sometimes contains free glycerol, which may cause errors, so removal of free glycerol in a sample is preferable. The removal method in the cases of Reaction Formulae 1 and 2 is different from that in the case of Reaction Formula 3. In the cases of Reaction Formulae 1 and 2, to remove free glycerol, an oxidizing enzyme (glycerol oxidase) that acts on glycerol is added to R1 to convert free glycerol into an aldehyde, thereby avoiding effects of free glycerol. In these cases, either or both of glycerol kinase and ATP should be added to R2. The glycerol oxidase may be a known glycerol oxidase such as glycerol oxidase derived from the genus *Aspergillus, Neurospora*, or *Penicillium* (see Agricultural Biological Chemistry 44(2), 399-406, 1980).

In the case of Reaction Formula 3, a test solution is added to Reagent 1 (R1) containing glycerol kinase, glycerol-3-phosphate oxidase, catalase, or peroxidase and a chromogen of a Trinder's reagent such as a phenol derivative, an aniline derivative, or a toluidine derivative, followed by heating, to thereby remove glycerol. Examples of the chromogen of a Trinder's reagent include chromogens described in Reaction Formula 1.

Reagent 2 (R2) includes a component containing the coupler such as 4-aminoantipyrine or 3-methyl-2-benzothiazolinone hydrazone (MBTH). Hydrogen peroxide is yielded at the time of mixing of R1 and R2 by a reaction of glycerol-3-phophate and produces a dye by oxidative condensation of Trinder's reagent and a coupler. The absorbance of the dye can be determined spectroscopically.

In the case of preparing a reagent for lipase activity determination using Reaction Formulae 1,2, and 3, a stabilizer of an enzyme such as: a sugar including sucrose, mannitol, sorbitol, maltose, lactose, cyclodextrin, trehalose; and a chelating agent including EDTA may be appropriately added, if necessary. The concentration of the sugar to be added may be in the range of 1 to 20%, and is preferably in the range of 3 to 15%, particularly preferably in the range of 4 to 8%. In the case of using a chelating agent, the concentration thereof may be in the range of 0.02 mM to 1 mM, and is preferably in the range of 0.05 mM to 0.5 mM, particularly preferably in the range of 0.1 to 0.3 mM. Moreover, various preservatives such as sodium azide may be appropriately added in an amount of 0.01 to 10%, preferably 0.05 to 1%. Furthermore, if necessary, the reagent may be divided into at least three reagents.

Meanwhile, a reagent for lipase determination of the present invention is stable in a liquid form, so it is not necessary to formulate the reagent by the freeze-drying method, thereby achieving extremely easy handling and excellent operability of the reagent. Meanwhile, the method of determining lipase activity has excellent accuracy and reproducibility. Specifically, in the case of Reaction Formula 1, it is a method of determining lipase activity including: converting a monoglyceride liberated from a diglyceride by a lipase reaction into glycerol by the action of monoglyceride lipase; converting glycerol into ADP by glycerol kinase in the presence of ATP; converting ADP into pyruvic acid by pyruvate kinase in the presence of phosphoenolpyruvate; allowing lactate dehydrogenase to act in the presence of reduced NAD; and determining the decrease rate of an absorbance of reduced NAD. The wavelength in determination of the absorbance of reduced NAD may be any wavelength where the pancreatic lipase activity in a sample can be determined accurately (it may be a certain wavelength or an integration of wavelengths in a range of certain wavelengths), but it is selected from, for example, preferably 300 to 400 nm, more preferably 320 to 360 nm, further preferably 330 to 350 nm, very preferably about 340 nm. The wavelength of about 340 nm means, for example, preferably a wavelength set to 340 nm with an error range of 10 nm or less, and the error range is more preferably 5 nm or less, further preferably 3 nm or less, very preferably 1 nm or less.

In the case of Reaction Formula 2, a method of determining lipase activity includes: converting a monoglyceride liberated from a diglyceride by a lipase reaction into glycerol by the action of monoglyceride lipase; converting glycerol into ADP by glycerol kinase in the presence of ATP; converting ADP into glucose-6-phosphate by ADP-dependent hexokinase in the presence of glucose; allowing glucose-6-phophate dehydrogenase to act in the presence of oxidized NAD or oxidized NADP; determining the increase rate of an absorbance of reduced NAD or reduced NADP. The wavelength in determination of the absorbance of reduced NAD may be any wavelength as long as pancreatic lipase activity in a sample can be determined accurately (it may be a certain wavelength or an integration of wavelengths in a range of certain wavelengths), but it is selected from, for example, preferably 300 to 400 nm, more preferably 320 to 360 nm, further preferably 330 to 350 nm, very preferably about 340 nm. The wavelength of about 340 nm means, for example, preferably a wavelength set to 340 nm with an error range of 10 nm or less, and the error range is more preferably 5 nm or less, further preferably 3 nm or less, very preferably 1 nm or less.

In the case of Reaction Formula 3, a monoglyceride liberated from a diglyceride by a lipase reaction is converted into glycerol by the action of monoglyceride lipase; glycerol is converted into glycerol-3-phosphate by glycerol kinase in the presence of ATP; and the resultant hydrogen peroxide can be converted by peroxidase, Trinder's reagent, and a coupler reagent into a quinone dye having a visible wavelength. The wavelength depends on the Trinder's reagent used, but a wavelength at about 540-700 nm should be selected. The increase rate of the generated dye may be determined by rate assay. Alternatively, after a reaction for a given length of time, the reaction is stopped with an enzyme-denaturing agent such as sodium lauryl sulfate, and the absorbance may be determined at a wavelength of about 540-700 nm.

After the intravenous injection of heparin or during the use of heparin for dialysis, lipases that appear in blood are hepatic lipase and lipoprotein lipase, and the above-described composition for lipase determination is used to determine the both enzymes simultaneously. In the case where specific determination of either of the enzymes is required, an inhibitor or an antibody that specifically inhibits the other lipase may be used to express the lipase specificity.

EXAMPLES

Hereinafter, the present invention will be described in more detail by way of examples but is not limited by the following examples.

Example 1-1

Preparation of Lipase Substrate Diglyceride

One point five gram of phosphatidylcholine derived from egg yolk lecithin (manufactured by Asahi Kasei Pharma Corporation) was dissolved in 10 ml of chloroform. Five mililiters of a 0.5 M PIPES-NaOH buffer (pH 7.5) in which 400 units of phospholipase C (manufactured by Asahi Kasei Pharma Corporation) had been dissolved was added thereto, and the mixture was stirred at 37° C. to perform a hydrolytic reaction. Two hours later, the solvent layer and aqueous layer were separated to collect the chloroform layer, and the layer was passed through a silica gel column (3 ml) that had been previously suspended in chloroform, followed by development with chloroform, to thereby yield a diglyceride fraction. Chloroform was completely distilled off using a rotary evaporator, to thereby yield 1.1 g of a diglyceride in an oil form.

Example 1-2

Preparation of a Composition for Pancreatic Lipase Activity Determination in Reaction Formula 2 Above (1) Preparation of Reagent 1 (R1)

There was prepared a reagent including 200 mM Bicine-NaOH (pH 8.0), 2 mM calcium chloride, 2 mM magnesium sulfate, 20 mM ammonium chloride, 3 mM adenosine triphosphate, 30 mM glucose, 3 mM NADP, 1,125 U/L monoglyceride lipase (manufactured by Asahi Kasei Pharma Corporation), 600 U/L glycerol kinase (manufactured by Asahi Kasei Pharma Corporation), 600 U/L glucose-6-phosphate dehydrogenase (manufactured by Toyobo Co., Ltd.), 900 U/L ADP-HK (manufactured by Asahi Kasei Pharma Corporation), and 15,000 U/L colipase (manufactured by Asahi Kasei Pharma Corporation).

(2) Preparation of Reagent 2 (R2)

A certain amount of the diglyceride yielded in Example 1-1 was weighed, and a certain amount of 0.04% POE nonylphenyl ether (1.5 mM MES-NaOH buffer, pH 5.5) was added to give 0.4 mM, followed by stirring at 37° C. for 30 minutes, to thereby yield a completely clear substrate solution. Deoxycholic acid was added to the substrate solution to give 8 mM, to thereby prepare Reagent 2.

Example 1-3

Preparation of a Composition for Non-pancreatic Lipase Activity Determination in Reaction Formula 3 Above (1) Preparation of Reagent 1 (R1)

There was prepared a reagent including 300 mM Tris-HCl buffer (pH 8.5), 2 mM calcium chloride, 3 mM magnesium sulfate, 3 mM adenosinetriphosphate, 1,125 U/L monoglyceride lipase (manufactured by Asahi Kasei Pharma Corporation), 600 U/L glycerol kinase (manufactured by Asahi Kasei Pharma Corporation), 30,000 U/L glycerol-3-phosphate oxidase (manufactured by Asahi Kasei Pharma Corporation), 5,000 U/L peroxidase (manufactured by Sigma), and 0.2% TOOS.

(2) Preparation of Reagent 2

There was prepared a reagent including a diglyceride substrate solution prepared by the method described in Example 1-2 (diglyceride concentration: 1.5 mM, POE-nonylphenyl ether concentration: 0.3%), 1 mM Bicine-NaOH (pH 8.0), and 0.2% 4-aminoantipyrine.

Example 1-4

Storage Stability of Lipase Substrate Diglyceride

A certain amount of the diglyceride yielded in Example 1-1 was weighed, and 0.5 to 200 mM Bicine-NaOH buffer (pH 8) containing 0.06% POE nonylphenyl ether was added so that the diglyceride concentration was 0.6 mM, followed by heating at 37° C. for 3 days. Then, the concentration of the remaining diglyceride was determined by an enzymatic method (0.1% sodiumazide was used as a preservative).

The results are shown in Table 1. The results shown in Table 1 revealed that the higher the concentration of the buffer, the lower the ratio of the remaining diglyceride substrate.

TABLE 1

| Buffer concentration (mM) | Ratio of remaining substrate (%) |
|---|---|
| 0.5 | 99.6 |
| 1 | 98.1 |
| 2.5 | 99.4 |
| 5 | 98.8 |
| 10 | 96.9 |
| 20 | 88.4 |
| 50 | 84.9 |
| 100 | 83.5 |
| 200 | 63.9 |

Example 1-5

Determination of Pancreatic Lipase Activity

Samples (0 to 50 microliters of enzyme solutions) were added to 1,000 microliters of Reagent 1 (R1) shown in Example 1-2, and the mixture was allowed to react at 37° C. for 3 minutes. Then, 500 microliters of Reagent 2 (R2) having the composition shown in Example 1-2 was added to start a reaction. Absorbances at 340 nm were determined sequentially. The linearity of absorbance changes to the enzyme amounts is shown in FIG. 1.

Example 1-6

Determination of Non-pancreatic Lipase Activity

To 1,000 microliters of Reagent 1 (R1) having the composition shown in Example 1-3 were added plasma samples 15 minutes after the intravenous injection of heparin, followed by incubation at 37° C. for 5 minutes. Thereafter, 500 microliters of R2 was added to start coloring reactions, and absorbances at 550 nm were determined sequentially. The linearity of absorbance changes to the enzyme amounts is shown in FIG. 2.

Example 2-1

Preparation of Diglyceride Substrate for Non-pancreatic Lipase Reaction

One point five gram of phosphatidylcholine derived from egg yolk lecithin (manufactured by Asahi Kasei Pharma Corporation) was dissolved in 10 ml of chloroform. Five milliliters of a 0.5 M PIPES-NaOH buffer (pH 7.5) in which 400 units of phospholipase C (manufactured by Asahi Kasei Pharma Corporation) had been dissolved was added thereto, and the mixture was stirred at 37° C. to perform a hydrolytic reaction. Two hours later, the solvent layer and aqueous layer were separated to collect the solvent layer, and the layer was charged into a wet silica gel column (3 ml), which had been previously prepared by suspending the gel in chloroform, followed by development with chloroform, to thereby yield a diglyceride fraction in the title.

Example 2-2-1

Preparation of Substrate Solution for Non-pancreatic Lipase Reaction

A certain amount of the diglyceride dissolved in chloroform yielded in Example 2-1 was taken, and the solvent was completely distilled off under reduced pressure. A certain amount of 2% POE-nonylphenyl ether (10 mM MES-NaOH buffer, pH 5.5) was added to give 10 mM, followed by stirring at 37° C. for 30 minutes, to thereby yield a substrate solution in the title as a completely clear substrate solution. The substrate solution was stored in refrigerator (about 4° C.).

Example 2-2-2

Preparation of an Alkaline-treated Substrate Solution for Non-pancreatic Lipase Reaction The procedure of Example 2-2-1 was repeated except that a buffer with a pH of 7.97 (Tris-HCl) was used instead of the buffer with a pH of 5.5 used in Example 2-2-1, to thereby yield a substrate solution in the title as a completely clear substrate solution. The substrate solution was stored in refrigerator (about 4° C.).

Example 2-3

Example of Coupling Enzyme System Based on Reaction Formula 1

Preparation of a Composition for Non-Pancreatic Lipase Activity Determination

A reagent including Reagent 1 (R1) and Reagent 2 (R2) was prepared as a composition for non-pancreatic lipase activity determination in the title.

(1) Preparation of Reagent 1 (R1)

There was prepared a reagent including 300 mM Bicine-NaOH (pH 8.0), a diglyceride substrate solution prepared by the method described in Example 2 (diglyceride concentration: 1.5 mM, POE-nonylphenyl ether concentration: 0.3%), 3 mM magnesium sulfate, 3 mM adenosine-3-phosphate, 1.5 mM phosphoenolpyruvate, 1,125 U/L monoglyceride lipase (manufactured by Asahi Kasei Pharma Corporation), 300 U/L glycerol kinase (manufactured by Asahi Kasei Pharma Corporation), 3,000 U/L pyruvate kinase (manufactured by Oriental Yeast Co., Ltd.), and 600 U/L lactate dehydrogenase (manufactured by Oriental Yeast Co., Ltd.).

(2) Preparation of Reagent 2 (R2)

There was prepared a reagent including 10 mM Bicine-NaOH (pH 8.5) and 1 mM reduced NAD.

Example 2-4

Example of Coupling Enzyme System Based on Reaction Formula 3

Preparation of a Composition for Non-pancreatic Lipase Activity Determination

A reagent including Reagent 1 (R1) and Reagent 2 (R2) was prepared as a composition for non-pancreatic lipase activity determination in the title.

(1) Preparation of Reagent 1 (R1)

There was prepared a reagent including 300 mM Bicine-NaOH (pH 8.0), a diglyceride substrate solution prepared by the method described in Examples 2-2-1 and 2-2-2 (diglyceride concentration: 1.5 mM, POE-nonylphenyl ether concentration: 0.3%), 3 mM magnesium sulfate, 30 mM ammonium chloride, 3 mM adenosine-3-phosphate, 1,125 U/L monoglyceride lipase (manufactured by Asahi Kasei Pharma Corporation), 300 U/L glycerol kinase (manufactured by Asahi Kasei Pharma Corporation), 15 U/ml glycerol-3-phosphate oxidase (manufactured by Asahi Kasei Pharma Corporation), 1,500 U/L peroxidase (manufactured by Sigma Corporation), and 0.2% TOOS.

(2) Preparation of Reagent 2 (R2)

There was prepared a reagent including 10 mM Bicine-NaOH (pH 8.0) and 0.2% 4-aminoantipyrine.

Example 2-5

Determination of Non-pancreatic Lipase Activity

Samples (0 to 50 microliters of enzyme solutions) were added to 800 microliters of Reagent 1 (R1) having the composition shown in Example 2-4, and the mixture was allowed to react at 37° C. for 3 minutes. Then, 400 microliters of Reagent 2 (R2) having the composition shown in Example 2-4 was added to perform a coloring reaction at 37° C. just for 5 minutes, and 500 microliters of 0.5% SDS (sodium lauryl sulfate) was added to stop the reaction, followed by determination of absorbances at 550 nm.

The dilution linearity of absorbance changes to the enzyme amounts (non-pancreatic lipase amounts) is shown in FIG. 3.

Example 2-6

Effect of Nonionic Surfactant on Pancreatic Lipase and Non-pancreatic Lipase Activities The effects of a nonionic surfactant were examined using ERM Lot. 1 certificated by Japanese Committee for Clinical Laboratory Standards as pancreatic lipase and using a lipase fraction (eluted with 0.8 M NaCl) purified by a heparin-Sepharose column from plasma after intravenous injection as non-pancreatic lipases. The results are shown in FIG. 4. In the range of 0.2% nonionic surfactant where the non-pancreatic lipase activity was activated to the maximum level, the pancreatic lipase activity was found not to be expressed at all.

Example 3-1

Preparation of Diglyceride Substrate for Pancreatic Lipase Reaction

One point five gram of purified phosphatidylcholine derived from egg yolk (manufactured by Asahi Kasei Pharma Corporation) was dissolved in 10 mL of chloroform. Five milliliters of 0.5 M PIPES-NaOH buffer (pH 7.5) in which 400 units of phospholipase C (manufactured by Asahi Kasei Pharma Corporation) had been dissolved was added thereto, and the mixture was stirred at 37° C. to perform a hydrolytic reaction. Two hours later, the solvent layer and aqueous layer were separated to collect the solvent layer, and the layer was charged into a wet silica gel column (3 ml), which had been previously prepared by suspending the gel in chloroform, followed by development with chloroform, to thereby yield a diglyceride fraction in the title.

Example 3-2

Preparation of Substrate Solutions for Pancreatic Lipase Reaction

A certain amount of the diglyceride dissolved in chloroform yielded in Example 3-1 was taken, and the solvent was completely distilled off under reduced pressure. A certain amount of 0.7% POE-nonylphenyl ether (15 mM various buffers) was added to give 7 mM, followed by heating at 37° C. for 10 hours under various pH conditions, to thereby yield substrate solutions in the title. The substrate solutions were stored in refrigerator (about 4° C.).

Example 3-3

Experiment for Determining Pancreatic Lipase Using the Substrates

Table 2 shows the levels of 1,3-DG production in the yielded substrates and the activities of pancreatic lipase determined by the method described in Example 3-5 using the substrate and reagents of the composition described in Example 3-5 (Reaction Formula 1).

As shown in Table 2, in the cases where the pH is 7 or lower, 1,3-diglyceride was not produced, and the activity values of pancreatic lipase were low.

TABLE 2

| pH | 1,3-DG (%) | Pancreatic lipase (%) |
|---|---|---|
| 4.52 | 0 | 75.6 |
| 5.04 | 0 | 87.2 |
| 7.28 | 20.9 | 100 |
| 7.97 | 50.3 | 99.1 |
| 8.51 | 60.2 | 98.9 |
| 9.12 | 61.7 | 99.6 |

Example 3-4

Method of Preparing the Substrate

A certain amount of the diglyceride dissolved in chloroform yielded in Example 3-1 was taken, and the solvent was completely distilled off under reduced pressure. A certain amount of 0.7% POE-nonylphenyl ether (2.5 mM buffer described in Table 3) was added to give 7 mM, and the mixture was allowed to stand, with heating at 37° C. for 1 hour and 4 hours. The 1,3-diglyceride contents were analyzed by the Yatoro scanning method. As shown in Table 3, in the cases of pH of 10 or higher, the equilibrium was achieved in 1 hour. In the cases of pH in the range of pH 7.88 to pH 9.33, the 1,3-glyceride contents were found to increase with the extension of the heating period.

TABLE 3

| Buffer | pH | 1,3 Diglyceride (%) 37° C., 1 h | 1,3 Diglyceride (%) 37° C., 4 h |
|---|---|---|---|
| Bicine-NaOH | 8.1 | 10.4 | 41.2 |
| Glycine-NaOH | 8.41 | 16.5 | 40.3 |
|  | 9.33 | 38.6 | 63.1 |
|  | 10.09 | 64.2 | 64.4 |
|  | 10.25 | 64.6 | 64.0 |
| Tris-HCl | 7.88 | 6.8 | 31.7 |
|  | 8.52 | 14.3 | 55.6 |
|  | 9.19 | 30.7 | 58.8 |

Example 3-5

Stability Experiment of the Substrate

The reagents of (Reaction Formula 3) were prepared by the conventional preparation method, that is, by the method described in Example 3-7 using, as raw materials: a pancreatic lipase substrate solution (pH 5.5), which had been subjected to a heating treatment for 1 hour with 1.05 mM egg yolk phosphatidylcholine-derived diglyceride solubilized with a solution containing 15 mM MES-NaOH (pH5.5) and 0.053% POE-nonylphenyl ether; and the substrate solution prepared in Example 3-2 under a condition of pH 7.97, and they were stored at 15° C. Determination was performed in accordance with the method of determining pancreatic lipase activity described in Example 3-7, and the results are shown in Table 4.

As shown in Table 4, the activity of the substrate was found to be very stable compared with that of the conventional substrate.

TABLE 4

| Reagent storage period | Substrate prepared at pH 9.7 | Conventional substrate (pH 5.5) |
|---|---|---|
| Immediately after preparation | 320 | 246 |
| Three days after | 322 | 274 |
| Ten days after | 318 | 307 |

Unit: [U/L]

Example 3-6

Example of Coupling Enzyme System Based on Reaction Formula 1

(I) Preparation of a Composition for Pancreatic Lipase Activity Determination

A reagent including Reagent 1 (R1) and Reagent 2 (R2) was prepared as a composition for pancreatic lipase activity determination in the title (1) Preparation of Reagent 1 (R1)

There was prepared a reagent including 300 mM Bicine-NaOH (pH 8.0), 15 mM Bicine-NaOH (pH 8.0), a pancreatic lipase substrate obtained by subjecting 1.05 mM egg yolk phosphatidylcholine-derived diglyceride solubilized with a solution containing 0.053% POE-nonylphenyl ether to a heating treatment at 37° C. for 10 hours, 3 mM magnesium sulfate, 30 mM ammonium chloride, 4,500 U/L colipase (manufactured by Asahi Kasei Pharma Corporation), 3 mM adenosine-3-phosphate, 1.5 mM phosphoenolpyruvate, 1,125 U/L monoglyceride lipase (manufactured by Asahi Kasei Pharma Corporation), 300 U/L glycerol kinase (manufactured by Asahi Kasei Pharma Corporation), 3,000 U/L pyruvate kinase (manufactured by Oriental Yeast Co., Ltd.), and 600 U/L lactate dehydrogenase (manufactured by Oriental Yeast Co., Ltd.).

(2) Preparation of Reagent 2 (R2)

There was prepared a reagent including 10 mM Bicine-NaOH (pH 8.5), 21 mM sodium deoxycholate, and 1 mM reduced NAD.

(II) Determination of Pancreatic Lipase Activity Using Autoanalyzer

Fifteen microliters of samples (ERM Lot. 1 certificated by Japanese Committee for Clinical Laboratory Standards) were added to 200 microliters of Reagent 1 (R1) having the composition shown in (I), and after a lapse of 5 minutes at 37° C., 100 microliters of Reagent 2 (R2) was added thereto to perform a reaction at 37° C., followed by sequential determination of absorbances (Abs) at 340 nm.

The activities of pancreatic lipase were calculated from the changes in absorbances from 3 minutes to 5 minutes after the addition of R2 by the following expression. The reaction time courses and dilution linearity are shown in FIG. 5 and FIG. 6, respectively.

Lipase activity (U/L)=change in absorbance at 340 nm per minute×1/6.3×315/15×1,000

Example 3-7

Example of Coupling Enzyme System Based on Reaction Formula 3

(I) Preparation of a Composition for Pancreatic Lipase Activity Determination

A reagent including Reagent 1 (R1) and Reagent 2 (R2) were prepared as a composition for pancreatic lipase activity determination in the title (1) Preparation of Reagent 1 (R1)

There was prepared a reagent including 300 mM Bicine-NaOH (pH 8.0), 15 mM Bicine-NaOH (pH 8.0), a pancreatic lipase substrate obtained by subjecting 1.05 mM egg yolk phosphatidylcholine-derived diglyceride solubilized with a solution containing 0.053% POE-nonylphenyl ether to a heating treatment at 37° C. for 10 hours, 3 mM magnesium sulfate, 30 mM ammonium chloride, 4,500 U/L colipase (manufactured by Asahi Kasei Pharma Corporation), 3 mM adenosinetriphosphate, 1,125 U/L monoglyceride lipase (manufactured by Asahi Kasei Pharma Corporation), 300 U/L glycerol kinase (manufactured by Asahi Kasei Pharma Corporation), 15 U/ml glycerol-3-phosphate oxidase (manufactured by Asahi Kasei Pharma Corporation), 1,500 U/L peroxidase (manufactured by Sigma Corporation), and 0.2% TOOS.

(2) Preparation of Reagent 2 (R2)

There was prepared a reagent including 10 mM Bicine-NaOH (pH 8.0), 21 mM sodium deoxycholate, and 0.2% 4-aminoantipyrine.

(II) Manual Determination of Pancreatic Lipase Activity 50 microliters of samples (ERM Lot. 1 certificated by Japanese Committee for Clinical Laboratory Standards) were added to 800 microliters of Reagent 1 (R1) having the composition shown in (I) to perform a reaction at 37° C. for 3 minutes, and 400 microliters of Reagent 2 (R2) having the composition shown in Example 3-6 was added to perform a coloring reaction at 37° C. just for 5 minutes. Then, 500 microliters of 0.5% SDS (sodium lauryl sulfate) was added to stop the reaction, and absorbances at 550 nm were determined. The dilution linearity was shown in FIG. 7.

INDUSTRIAL APPLICABILITY

The composition for lipase activity determination of the present invention enables accurate determination of lipase activity and is suitable as a diagnostic reagent of lipase activity in blood.

The invention claimed is:

1. A diglyceride solution for lipase activity determination, comprising at least one diglyceride, a buffer having a concentration of 0.5 to 7 mM, and a nonionic surfactant, wherein an activity of the at least one diglyceride in a lipase assay, when stored at 15° C. for three days, differs by no more than about 1% of the activity of the at least one diglyceride in the lipase assay immediately after preparation of the diglyceride solution.

2. The diglyceride solution for lipase activity determination according to claim 1, wherein the at least one diglyceride comprises a mixture of 1,3-diglyceride and 1,2-diglyceride.

3. The solution according to claim 1, comprising a buffer having a concentration of 2 to 7 mM.

4. The solution according to claim 3, comprising a buffer having a concentration of 3 to 5 mM.

5. The solution according to claims 4, wherein the pH of the buffer is in the range of from 5 to 9.5.

6. The solution according to claim 5, wherein the buffer is selected from the group consisting of MES, Bis-Tris, ADA, PIPES, ACES, MOPSO, BES, MOPS, TES, HEPES, DIPSO, TAPSO, POPSO, HEPPSO, EPPS, Tricine, Bicine, TAPS, CHES, CAPSO, and CAPS.

7. The solution according to claim 6, wherein the buffer is Bicine.

8. The solution according to claim 6, wherein the nonionic surfactant is a polyoxyethylene alkylphenyl ether nonionic surfactant.

9. The solution according to claim 8, wherein the polyoxyethylene alkylphenyl ether nonionic surfactant is polyoxyethylene nonylphenyl ether.

10. The solution according to claim 8, wherein the concentration of the polyoxyethylene alkylphenyl ether nonionic surfactant is 0.15% to 2%.

11. A composition for lipase activity determination, comprising at least one enzyme that converts a monoglyceride liberated from a diglyceride by a lipase reaction, into glycerol-3-phosphate, via free glycerol, wherein the diglyceride is from a diglyceride solution comprising the diglyceride, a buffer having a concentration of 0.5 to 7 mM, and a nonionic surfactant, wherein an activity of the diglyceride in a lipase assay, when stored at 15° C. for three days, differs by no more than about 1% of the activity of the diglyceride in the lipase assay immediately after preparation of the diglyceride solution.

12. A kit for non-pancreatic lipase activity determination, comprising: (1) Reagent 1 containing at least a buffer having a concentration of 50 mM to 500 mM, monoglyceride lipase, ATP, glycerol kinase, glycerol-3-phosphate oxidase, and peroxidase; and (2) Reagent 2 containing at least a diglyceride solution for lipase activity determination comprising at least one diglyceride, a buffer having a concentration of 0.5 to 7 mM, and a nonionic surfactant, wherein an activity of the at least one diglyceride in a lipase assay, when stored at 15° C. for three days, differs by no more than about 1% of the activity of the at least one diglyceride in the lipase assay immediately after preparation of the diglyceride solution.

13. The kit for non-pancreatic lipase activity determination according to claim 12, wherein the concentration of the nonionic surfactant is one that does not allow the expression of lipase activity of pancreatic lipase and causes the expression of lipase activity of non-pancreatic lipases.

14. The kit for non-pancreatic lipase activity determination according to claim 12, wherein Reagent 1 and/or Reagent 2 is in liquid form.

15. A kit for non-pancreatic lipase activity determination, comprising: (1) Reagent 1 containing at least a buffer having a concentration of 50 mM to 500 mM, monoglyceride lipase, ATP, glycerol kinase, oxidized NAD or oxidized NADP, glucose, ADP-dependent hexokinase, and glucose-6-phosphate dehydrogenase; and (2) Reagent 2 containing at least a diglyceride solution for lipase activity determination comprising at least one diglyceride, a buffer having a concentration of 0.5 to 7 mM, and a nonionic surfactant, wherein an activity of the at least one diglyceride in a lipase assay, when stored at 15° C. for three days, differs by no more than about 1% of the activity of the at least one diglyceride in the lipase assay immediately after preparation of the diglyceride solution.

16. A kit for non-pancreatic lipase activity determination, comprising: (1) Reagent 1 containing at least a buffer having a concentration of 50 mM to 500 mM, monoglyceride lipase, ATP, glycerol kinase, reduced NAD, phosphoenolpyruvate, pyruvate kinase, and lactate dehydrogenase; and (2) Reagent 2 containing at least a diglyceride solution for lipase activity determination comprising at least one diglyceride, a buffer having a concentration of 0.5 to 7 mM, and a nonionic surfactant, wherein an activity of the at least one diglyceride in a lipase assay, when stored at 15° C. for three days, differs by no more than about 1% of the activity of the at least one diglyceride in the lipase assay immediately after preparation of the diglyceride solution.

17. A kit for pancreatic lipase activity determination, comprising:
(1) Reagent 1 containing at least a diglyceride solution for lipase activity determination comprising at least one diglyceride, a buffer having a concentration of 0.5 to 7 mM, and a nonionic surfactant, wherein an activity of the at least one diglyceride in a lipase assay, when stored at 15° C. for three days, differs by no more than about 1% of the activity of the at least one diglyceride in the lipase assay immediately after preparation of the diglyceride solution, monoglyceride lipase, ATP, glycerol kinase, glycerol-3-phosphate oxidase, and peroxidase; and
(2) Reagent 2 containing at least a buffer having a concentration of 50 mM to 500 mM and bile acid or a salt thereof.

18. The kit for pancreatic lipase activity determination according to claim 17, wherein the concentration of the nonionic surfactant is one that does not allow the expression of lipase activity of non-pancreatic lipases and causes the expression of lipase activity of pancreatic lipase.

19. The kit for pancreatic lipase activity determination according to claim 17, wherein Reagent 1 and/or Reagent 2 is in a liquid form.

20. A kit for pancreatic lipase activity determination, comprising:
(1) Reagent 1 containing at least a diglyceride solution for lipase activity determination comprising at least one diglyceride, a buffer having a concentration of 0.5 to 7 mM, and a nonionic surfactant, wherein an activity of the at least one diglyceride in a lipase assay, when stored at 15° C. for three days, differs by no more than about 1% of the activity of the at least one diglyceride in the lipase assay immediately after preparation of the diglyceride solution, monoglyceride lipase, ATP, glycerol kinase, oxidized NAD or oxidized NADP, glucose, ADP-dependent hexokinase, and glucose-6-phosphate dehydrogenase; and (2) Reagent 2 containing at least a buffer having a concentration of 50 mM to 500 mM and bile acid or a salt thereof.

21. A kit for pancreatic lipase activity determination, comprising:
(1) Reagent 1 containing at least a diglyceride solution for lipase activity determination comprising at least one diglyceride, a buffer having a concentration of 0.5 to 7 mM, and a nonionic surfactant, wherein an activity of the at least one diglyceride in a lipase assay, when stored at 15° C. for three days, differs by no more than about 1% of the activity of the at least one diglyceride in the lipase assay immediately after preparation of the diglyceride solution, monoglyceride lipase, ATP, glycerol kinase, reduced NAD, phosphoenolpyruvate, pyruvate kinase, and lactate dehydrogenase; and (2) Reagent 2 containing at least a buffer having a concentration of 50 mM to 500 mM and bile acid or a salt thereof.

* * * * *